(12) United States Patent
Connolly et al.

(10) Patent No.: US 10,065,953 B2
(45) Date of Patent: Sep. 4, 2018

(54) IMIDAZO[1,2-A]PYRIDINE DERIVATIVES FOR USE AS INHIBITORS OF HUMAN IMMUNODEFICIENCY VIRUS REPLICATION

(71) Applicant: ViiV Healthcare UK (No.5) Limited, Brentford, Middlesex (GB)

(72) Inventors: Timothy P. Connolly, Wallingford, CT (US); Kyle J. Eastman, Wallingford, CT (US); B. Narasimhulu Naidu, Wallingford, CT (US); Kevin Peese, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 28 days.

(21) Appl. No.: 15/505,955

(22) PCT Filed: Aug. 25, 2015

(86) PCT No.: PCT/US2015/046648
§ 371 (c)(1),
(2) Date: Feb. 23, 2017

(87) PCT Pub. No.: WO2016/033009
PCT Pub. Date: Mar. 3, 2016

(65) Prior Publication Data
US 2018/0222901 A1   Aug. 9, 2018

Related U.S. Application Data

(60) Provisional application No. 62/042,300, filed on Aug. 27, 2014.

(51) Int. Cl.
| | | |
|---|---|---|
| *C07D 401/02* | (2006.01) |
| *C07D 401/10* | (2006.01) |
| *A61K 31/4353* | (2006.01) |
| *A61K 31/437* | (2006.01) |
| *C07D 471/04* | (2006.01) |
| *A61P 31/18* | (2006.01) |
| *C07D 519/00* | (2006.01) |

(52) U.S. Cl.
CPC ............ *C07D 471/04* (2013.01); *A61P 31/18* (2018.01); *C07D 519/00* (2013.01)

(58) Field of Classification Search
CPC .. C07D 401/02; C07D 401/10; A61K 31/437; A61K 31/4353
USPC .......................................... 514/300; 546/121
See application file for complete search history.

(56) References Cited

U.S. PATENT DOCUMENTS 9,655,889 B2 * 5/2017 Peese ................... C07D 471/04

FOREIGN PATENT DOCUMENTS

| WO | WO 2010/130034 A1 | 11/2010 |
| WO | WO 2013/134113 A1 | 9/2013 |
| WO | WO 2014/164409 A1 | 10/2014 |

* cited by examiner

*Primary Examiner* — Niloofar Rahmani
(74) *Attorney, Agent, or Firm* — Robert H. Brink; Edward R. Gimmi; William R. Majarian

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

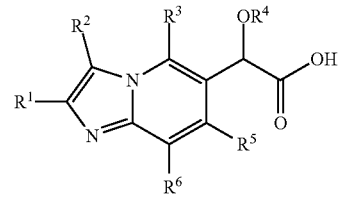

10 Claims, No Drawings

IMIDAZO[1,2-A]PYRIDINE DERIVATIVES FOR USE AS INHIBITORS OF HUMAN IMMUNODEFICIENCY VIRUS REPLICATION

CROSS-REFERENCE TO RELATED APPLICATIONS

This application is a § 371 of International Application No. PCT/US2015/046648, filed 25 Aug. 2015, which claims the benefit of U.S. Provisional Application No. 62/042,300, filed 27 Aug. 2014, which are incorporated herein in their entireties.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 35.3 million people worldwide are infected with the virus (UNAIDS Report on the Global AIDS Epidemic 2013). In addition to the large number of individuals already infected, the virus continues to spread. Estimates from 2012 point to close to 3.4 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2012033735, WO2013123148, WO2013134113, and WO20140028384.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

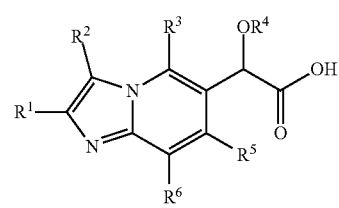

where:
R$^1$ is phenyl substituted with Ar$^1$ substituent and also substituted with 0-3 substituents selected from halo, cyano, alkyl, haloalkyl, alkoxy, haloalkoxy, and alkenyloxy;
R$^2$ is hydrogen or alkyl;
R$^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or R$^3$ is cycloalkyl, cycloalkenyl, phenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
R$^4$ is alkyl or haloalkyl;
R$^5$ is hydrogen or alkyl;
R$^6$ is hydrogen or alkyl;
Ar$^1$ is phenyl, pyridinyl, pyridazinyl, pyrimidinyl, pyrazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, or tetrazolyl, and is substituted with 0-3 substituents selected from halo, cyano, alkyl, haloalkyl, benzyl, alkoxy, haloalkoxy, alkenyloxy, and benzyloxy;

or a pharmaceutically acceptable salt thereof.

Another aspect of the invention is a compound of formula I where:
$R^1$ is phenyl substituted with $Ar^1$ substituent;
$R^2$ is hydrogen;
$R^3$ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or $R^3$ is phenyl, chromanyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
$R^4$ is alkyl;
$R^5$ is alkyl;
$R^6$ is hydrogen;
$Ar^1$ is phenyl or pyrazolyl, and is substituted with 0-3 substituents selected from halo, cyano, alkyl, haloalkyl, benzyl, alkoxy, haloalkoxy, alkenyloxy, and benzyloxy; or a pharmaceutically acceptable salt thereof.

Another aspect of the invention is a compound of formula I where $R^1$ is phenyl substituted with $Ar^1$ substituent.

Another aspect of the invention is a compound of formula I where $R^2$ is hydrogen, $R^4$ is alkyl, $R^5$ is alkyl, and $R^6$ is hydrogen.

Another aspect of the invention is a compound of formula I where $R^3$ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of formula I where $R^3$ is phenyl, chromanyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of formula I where $Ar^1$ is phenyl, pyridinyl, pyridazinyl, pyrimidinyl, or pyrazinyl, and is substituted with 0-3 substituents selected from halo, cyano, alkyl, haloalkyl, benzyl, alkoxy, haloalkoxy, alkenyloxy, and benzyloxy.

Another aspect of the invention is a compound of formula I where $Ar^1$ is phenyl substituted with 0-3 substituents selected from halo, cyano, alkyl, haloalkyl, alkoxy, haloalkoxy, alkenyloxy, and benzyloxy.

Another aspect of the invention is a compound of formula I where $Ar^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, or tetrazolyl, and is substituted with 0-3 substituents selected from halo, cyano, alkyl, haloalkyl, benzyl, alkoxy, haloalkoxy, alkenyloxy, and benzyloxy.

Another aspect of the invention is a compound of formula I where $Ar^1$ is pyrazolyl substituted with 0-3 substituents selected from halo, cyano, alkyl, haloalkyl, benzyl, alkoxy, haloalkoxy, alkenyloxy, and benzyloxy.

For a compound of Formula I, the scope of any instance of a variable substituent, including $R^1$, $R^2$, $R^3$, $R^4$, $R^5$, $R^6$, and $Ar^1$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes fluoro, chloro, bromo, and iodo. "Halo" includes all halogenated isomers from monohalo substituted to perhalo substituted in substituents defined with halo, for example, "Haloalkyl" and "haloalkoxy", "halophenyl", "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R. The structures described are intended to encompass physically stable compounds which are understood by those skilled in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication.

A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVS-Venv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 1. Activity equal to A refers to a compound having an $EC_{50} \leq 100$ nM, while B and C denote compounds having an $EC_{50}$ between 100 nM and 1 uM (B) or >1 uM (C).

TABLE 1

| Example | $EC_{50}$ µM |
|---|---|
| 1 | 0.051 |
| 2 | 0.032 |
| 3 | 0.026 |
| 4 | 0.021 |
| 5 | 0.029 |
| 6 | 0.021 |
| 7 | 0.006 |
| 8 | 0.022 |
| 9 | 0.006 |
| 10 | 0.007 |
| 11 | 0.021 |
| 12 | 0.019 |
| 13 | 0.398 |
| 14 | 0.020 |
| 15 | 0.175 |
| 16 | 0.004 |
| 17 | 0.159 |
| 18 | 0.007 |
| 19 | 0.095 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV entry inhibitors, HIV attachment inhibitors, HIV integrase inhibitors, pharmacokinetic enhancers, and combinations or these agents.

Another aspect of the invention is a method wherein the agent is a nucleoside HIV reverse transcriptase inhibitor. Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine.

Another aspect of the invention is a method wherein the agent is a non-nucleoside HIV reverse transcriptase inhibitor. Another aspect of the invention is a method wherein the non-nucleoside HIV reverse transcriptase inhibitor is selected from the group consisting of delavirdine, efavirenz, etrivirine, nevirapine, and rilpivirine.

Another aspect of the invention is a method wherein the agent is an HIV protease inhibitor. Another aspect of the invention is a method wherein the HIV protease inhibitor is selected from the group consisting of amprenavir, atazanavir, darunavir, fosamprenavir, indinavir, lopinavir, nelfinavir, ritonavir, saquinavir and, tipranavir.

Another aspect of the invention is a method wherein the agent is an HIV fusion inhibitor. Another aspect of the invention is a method wherein the HIV fusion inhibitor is enfuvirtide or T-1249.

Another aspect of the invention is a method wherein the agent is an HIV entry inhibitor. Another aspect of the invention is a method wherein the HIV entry inhibitor is maraviroc.

Another aspect of the invention is a method wherein the agent is an HIV integrase inhibitor. Another aspect of the invention is a method wherein the HIV integrase inhibitor is dolutegravir, elvitegravir, or raltegravir.

Another aspect of the invention is a method wherein the agent is an HIV attachment inhibitor.

Another aspect of the invention is a method wherein the agent is an HIV budding or maturation inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is a pharmaceutical composition with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV entry inhibitors, HIV attachment inhibitors, HIV integrase inhibitors, pharmacokinetic enhancers, and combinations or these agents.

Another aspect of the invention is a pharmaceutical composition the agent is a nucleoside HIV reverse transcriptase inhibitor. Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine.

Another aspect of the invention is a pharmaceutical composition wherein the agent is a non-nucleoside HIV reverse transcriptase inhibitor. Another aspect of the invention is a method wherein the non-nucleoside HIV reverse transcriptase inhibitor is selected from the group consisting of delavirdine, efavirenz, etrivirine, nevirapine, and rilpivirine.

Another aspect of the invention is a pharmaceutical composition wherein the agent is an HIV protease inhibitor. Another aspect of the invention is a method wherein the HIV protease inhibitor is selected from the group consisting of amprenavir, atazanavir, darunavir, fosamprenavir, indinavir, lopinavir, nelfinavir, ritonavir, saquinavir and, tipranavir.

Another aspect of the invention is a pharmaceutical composition wherein the agent is an HIV fusion inhibitor. Another aspect of the invention is a method wherein the HIV fusion inhibitor is enfuvirtide or T-1249.

Another aspect of the invention is a pharmaceutical composition wherein the agent is an HIV entry inhibitor. Another aspect of the invention is a method wherein the HIV entry inhibitor is maraviroc.

Another aspect of the invention is a pharmaceutical composition wherein the agent is an HIV integrase inhibitor. Another aspect of the invention is a method wherein the HIV integrase inhibitor is dolutegravir, elvitegravir, or raltegravir.

Another aspect of the invention is a pharmaceutical composition wherein the agent is an HIV attachment inhibitor.

Another aspect of the invention is a pharmaceutical composition wherein the agent is an HIV budding or maturation inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for 30 minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "L" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds of this invention can be synthesized from an appropriately substituted heterocycle I-1 according to Schemes I-III. Acid mediated hydrolysis of nitrile I-1 provide carboxylic acid I-2 which was esterified using tet-butyle acetate and perchloric acid to give ester I-3. Palladium mediated coupling of imine I-4 to I-3 followed by cleavage of benzophenone using hydroxylamine and ammonium acetate furnished aminopyridine I-5. Condensation of I-5 with beomide I-6 gave the bicyclic compound I-7 which is transformed to the carboxylic acid I-8 by treating with HCl-dioxane. The caboxylic acid was converted to ketoester I-9 by following the method of Bode et al (*J. Am. Chem. Soc.* 2008, 130, 4253-4255).

Scheme I
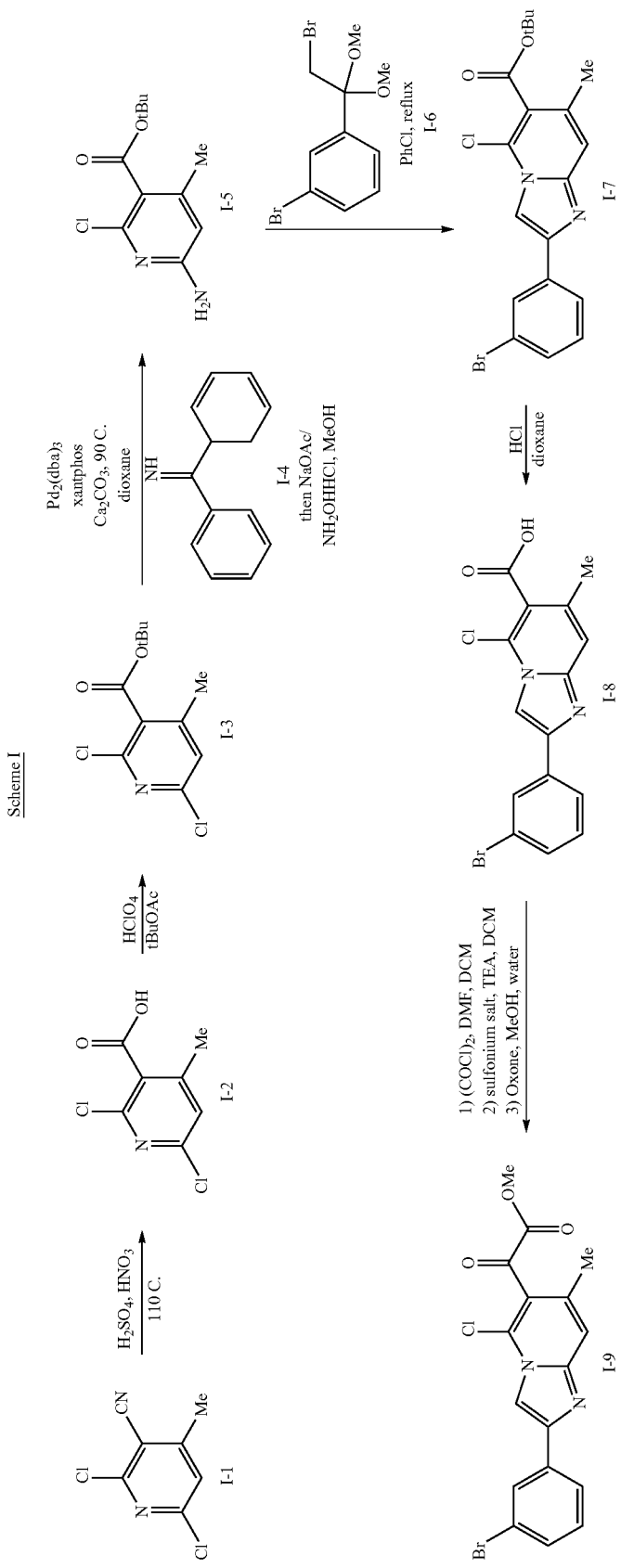

Addition of piperidine II-1 to The keto ester I-9 provided intermediate II-2 which is reduced to chiral alcohol II-3 using well-known conditions in the presence of catalytic chiral Lewis acid. Alcohol II-3 is converted to the intermediates II-4 by well-known conditions, including but not limited to isobutylene and perchloric acid. The intermediate II-4 is transformed to intermediate compounds II-5 by coupling appropriate aryl derivative using conditions well known in the literature. Saponification of Intermediate provided the desired caboxylic acid II-6.

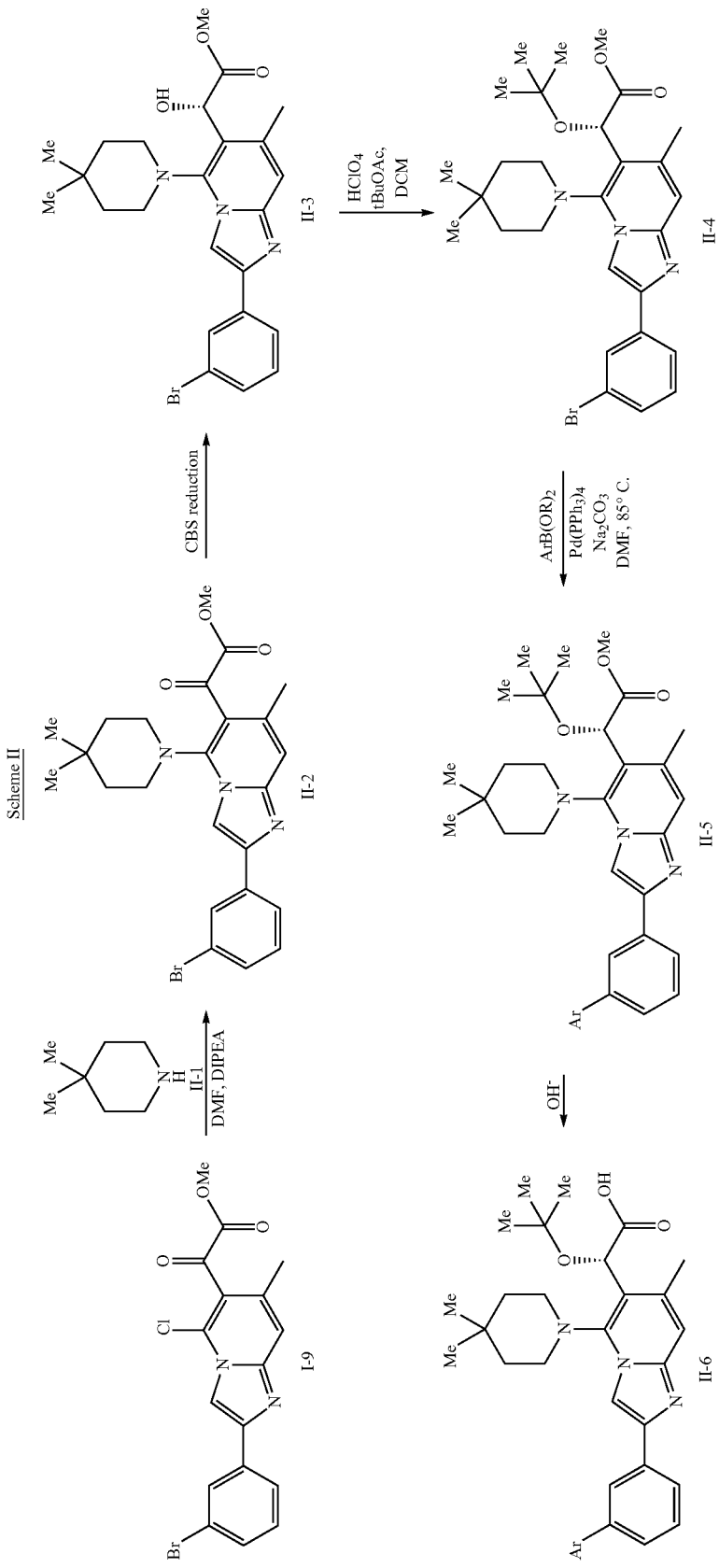

The keto ester intermediate I-9 is reduced to chiral alcohol III-1 using well-known conditions in the presence of catalytic chiral Lewis acid. Intermediate III-1 is converted to the intermediate III-2 by well-known conditions, including but not limited to isobutylene and perchloric acid. The intermediate II-2 is transformed to intermediate II-4 by iterative coupling of arylboronate derivatives by using conditions well known in the literature. Saponification of ester III-4 provided the final carboxylic acid III-5.

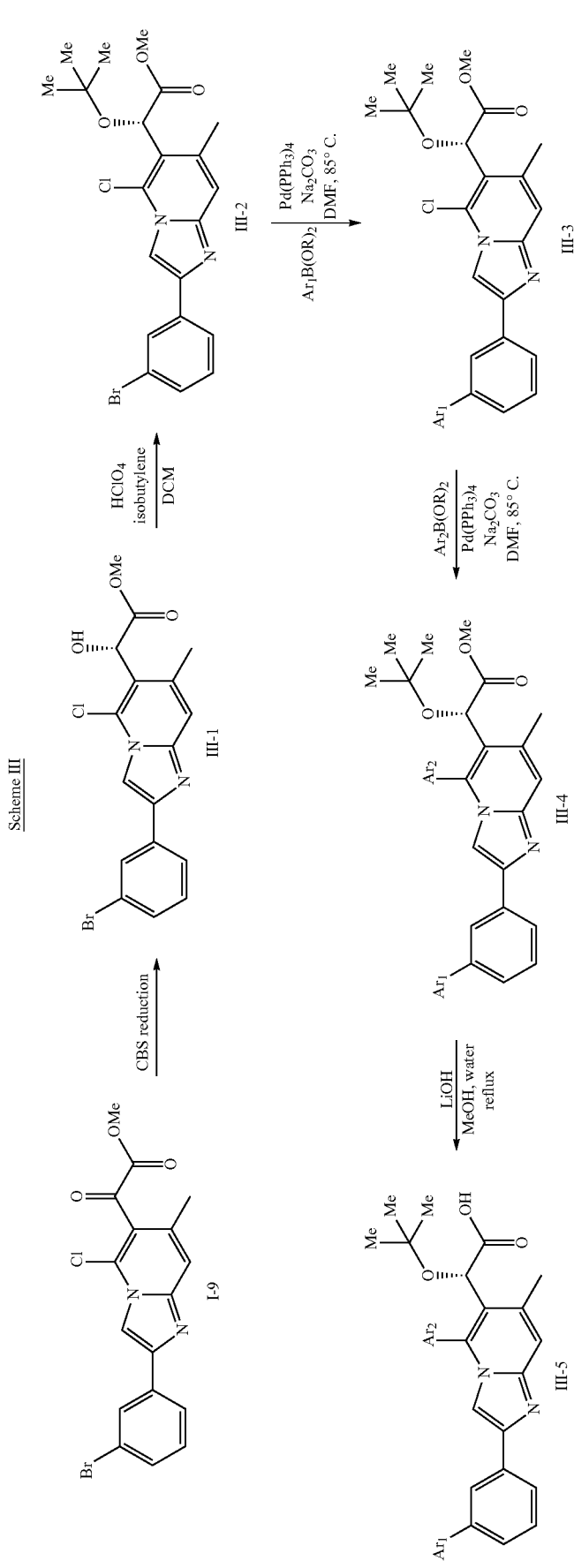

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 9:1 H₂O/acetonitrile with 10 mM NH₄OAc and mobile phase B: A: 9:1 acetonitrile/H₂O with: 10 mM NH₄OAc or mobile phase A: 95:5 H₂O/MeOH with 20 mM NH₄OAc and mobile phase B: 95:5 MeOH/H₂O with 20 mM NH₄OAc.

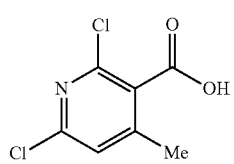

Intermediate 1

2,6-Dichloro-4-methylnicotinic Acid

Prepared from commercially available 2,6-dichloro-4-methylnicotinonitrile following procedure in U.S. Pat. No. 6,677,352 (2004).

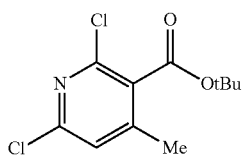

Intermediate 2 tert-Butyl 2,6-dichloro-4-methylnicotinate

To a solution of 2,6-dichloro-4-methylnicotinic acid (1.00 g, 4.85 mmol, 1 equiv) in tert-butyl acetate (24 mL) was added 70% perchloric acid (0.88 mL, 14.56 mmol, 3 equiv). After 1 h, reaction was diluted with DCM, washed cautiously with saturated aqueous sodium bicarbonate solution, dried (Na₂SO₄), and concentrated in vacuo to provide the product (1.21 g, 95%) as a pale yellow oil. 1H NMR (400 MHz, CDCl₃) δ 7.15 (s, 1H), 2.37 (d, J=0.5 Hz, 3H), 1.62 (s, 9H); LCMS (ESI, M+1): 262.1.

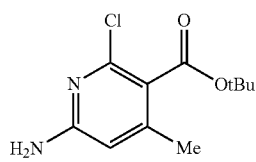

Intermediate 3 tert-Butyl 6-amino-2-chloro-4-methylnicotinate tert-Butyl 2,6-dichloro-4-methylnicotinate (10.5 g, 40.1 mmol, 1 equiv), Pd₂(dba)₃ (1.84 g, 2.01 mmol, 0.05 equiv), xantphos (2.32 g, 4.01 mmol, 0.1 equiv), and Cs₂CO₃ slurried in dioxane (deoxygenated by bubbling nitrogen through it for 10 min). Benzophenone imine (8.0 mL, 48.1 mmol, 1.2 equiv) added and the mixture was heated at 90° C. for 1 h. Upon cooling to ambient temperature, the reaction was diluted with EtOAc and washed with water, dried (Na₂SO₄), and concentrated in vacuo. The crude product was taken up in MeOH (200 mL) and NaOAc (9.87, 120 mmol, equiv) and hydroxylamine hydrochloride (5.57 g, 80 mmol, 2 equiv) was added. After 30 min, the reaction was added to 1 N NaOH and extracted with DCM (×2). The combined DCM extracts were dried (Na₂SO₄) and concentrated in vacuo. The crude product was purified by flash column chromatography (0-30% EtOAc/hex) to afford tert-butyl 6-amino-2-chloro-4-methylnicotinate (7.5 g, 77%). ¹H NMR (400 MHz, CDCl₃) δ 6.22 (d, J=0.8 Hz, 1H), 4.58 (br. s., 2H), 2.27 (d, J=0.8 Hz, 3H), 1.60 (s, 9H); LCMS (ESI, M+1): 243.1.

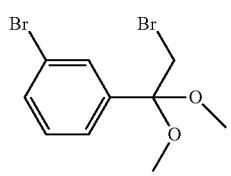

Intermediate 4

1-Bromo-3-(2-bromo-1,1-dimethoxyethyl)benzene

A solution of 2-bromo-1-(3-bromophenyl)ethanone (48.23 g, 174 mmol) in MeOH (200 ml) was treated with trimethyl orthoformate (57.5 mL) and pTsOH (1.650 g, 8.68 mmol) and heated at reflux (75° C. oil bath) under nitrogen for 2.5 hrs. The mixture was cooled, concentrated to a viscous oil, diluted with Et₂O (250 mL), and washed with 2.0 M aq. K₂CO₃ (100 mL), then brine. The organic layer was dried (MgSO₄), filtered, and concentrated under reduced pressure, affording the product (56.43 g, 174 mmol, 100% yield) as a mobile yellow oil. ¹H NMR (500 MHz, CDCl₃) δ 7.69 (t, J=1.8 Hz, 1H), 7.48 (ddd, J=7.9, 2.0, 1.0 Hz, 1H), 7.43 (dq, J=7.8, 0.9 Hz, 1H), 7.29-7.24 (m, 2H), 3.60 (s, 2H), 3.24 (s, 6H). ¹³C NMR (126 MHz, CDCl₃) δ 141.0, 131.5, 130.6, 129.6, 125.9, 122.3, 100.8, 49.5, 35.0. LCMS (M+H-MeOH)=291.97.

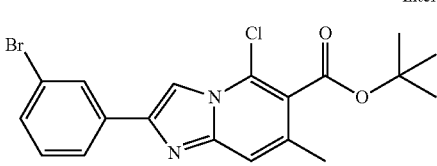

Intermediate 5 tert-Butyl 2-(3-bromophenyl)-5-chloro-7-methylimidazo[, 2-a]pyridine-6-carboxylate A flask charged with chlorobenzene (300 ml) was heated to reflux (140° C. oil bath) and to this was added sequentially 1-bromo-3-(2-bromo-1,1-dimethoxyethyl)benzene (56.05 g, 173 mmol) as an oil, and tert-butyl 6-amino-2-chloro-4-methylnicotinate (33.91 g, 140 mmol) as a powder, rinsing both with additional chlorobenzene (70 mL total) to facilitate transfer. The reaction was returned to reflux and heated for 90 min, then cooled and poured slowly into vigorously stirred Et₂O (1500 mL). The resulting suspension was stirred for 15 min, then solids were collected by vacuum filtration to afford the product (47 g, 111 mmol, 64.4% yield) as a tan powdery solid. A 3 g sample of product was first purified by biotage (80 g SiO$_2$, 0% (3 CV), 0-60% (15 CV), 60% (2 CV), EtOAc in hexanes), then recrystallized from hot acetonitrile to afford a high purity sample for spectra. 1H NMR (500 MHz, CDCl$_3$) δ 8.14 (t, J=1.7 Hz, 1H), 8.02 (d, J=0.5 Hz, 1H), 7.89 (dq, J=7.7, 0.9 Hz, 1H), 7.48 (ddd, J=8.0, 2.0, 1.1 Hz, 1H), 7.41-7.39 (m, 1H), 7.32 (t, J=7.9 Hz, 1H), 2.45 (d, J=0.9 Hz, 3H), 1.65 (s, 9H). $^{13}$C NMR (126 MHz, CDCl$_3$) δ 164.3, 145.6, 145.2, 135.3, 133.6, 131.3, 130.3, 129.2, 124.7, 123.9, 123.0, 121.7, 115.4, 107.6, 83.9, 28.1, 19.9. LCMS (M+H)=421.3.

Intermediate 6

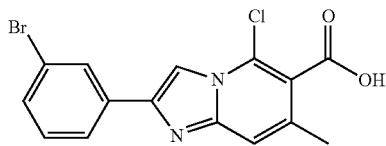

2-(3-Bromophenyl)-5-chloro-7-methylimidazo[, 2-a]pyridine-6-carboxylic Acid.HCl Salt A suspension of tert-butyl 2-(3-bromophenyl)-5-chloro-7-methylimidazo[1,2-a]pyridine-6-carboxylate (35.5 g, 84 mmol) in 4.0 N HCl in dioxane (800 ml) was stirred for 48 hrs. The reaction was concentrated to a thick paste, then the residue was triturated with acetonitrile, collecting solids by vacuum filtration and washing with several small portions of acetonitrile. The reside was resuspended in fresh acetonitrile, stirred for 20 min, then filtered to collect solids. The solids were dried once from Et$_2$O by rotary evaporator, to afford the product (23.3 g, 58.0 mmol, 68.8% yield) as an off-white powder. 1H NMR (500 MHz, DMSO-d$_6$) δ 8.90 (s, 1H), 8.35 (t, J=1.7 Hz, 1H), 8.17-8.08 (m, 1H), 7.73 (s, 1H), 7.67-7.59 (m, 1H), 7.48 (t, J=8.0 Hz, 1H), 2.46 (d, J=0.9 Hz, 3H). $^{13}$C NMR (126 MHz, DMSO-d$_6$) δ 165.9, 143.1, 132.6, 131.7, 129.2, 125.6, 125.1, 125.1, 124.3, 123.0, 113.2, 110.9, 66.8, 20.0. LCMS (M+H)=367.1

Intermediate 7

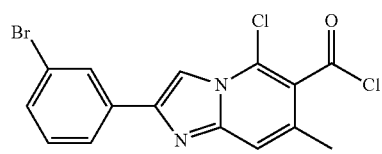

2-(3-Bromophenyl)-5-chloro-7-methylimidazo[1,2-a]pyridine-6-carbonyl chloride

A suspension of 2-(3-bromophenyl)-5-chloro-7-methyl-imidazo[1,2-a]pyridine-6-carboxylic acid, HCl salt (22.03 g, 60.3 mmol) in dry dichlormethane (600 ml) was treated with oxalyl chloride (13 ml, 149 mmol) followed by DMF (1.5 mL). The suspension was stirred for 3.5 hrs, then concentrated under reduced pressure to afford the acid-chloride as a brown powdery solid which was then used immediately in the following step.

Intermediate 8

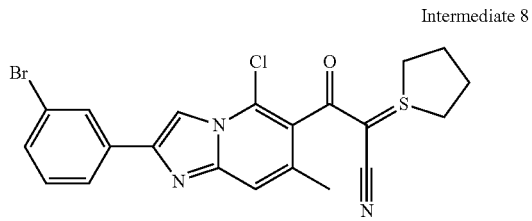 [SMILES: Cc1cc2nc(-c3cccc(Br)c3)cn2c(Cl)c1C(=O)C(C#N)=S1CCCC1]

3-[2-(3-Bromophenyl)-5-chloro-7-methylimidazo[1,2-a]pyridin-6-yl]-3-oxo-2-[(1E)-1λ$^4$-thiolan-1-ylidene]propanenitrile A stirred solution of 2-(3-bromophenyl)-5-chloro-7-methylimidazo[1,2-a]pyridine-6-carbonyl chloride (23.16 g, 60.3 mmol) in dichloromethane (600 ml) was treated with 1-(cyanomethyl)tetrahydro-1H-thiophen-1-ium bromide (18.82 g, 90 mmol, ref: J. Am. Che. Sco. 2008, 130, 4253) followed by Hunig's Base (31.6 ml, 181 mmol). The reaction was stirred for 16 hrs at room temperature, then the mixture was washed with saturated sodium bicarbonate solution (2×200 mL) and the combined aqueous layer was back extracted (2×50 mL). The combined organic layers were dried (Na$_2$SO$_4$), filtered, and concentrated under reduced pressure to a reduced volume. The concentrated solution was purified by biotage (330 g SiO$_2$, 10% (3 CV), 10-100% (10 CV), 100% (2 CV), EtOAc in hexanes, then 0% (2 CV), 0-10% (10 CV), 10% (2 CV) MeOH in CH$_2$Cl$_2$). Product fractions were pooled and concentrated under reduced pressure, affording the product (24.6 g, 51.8 mmol, 86% yield) as a brown glassy solid. This material was used as-is in the following step. Separately, a small sample of column purified product was dissolved in minimal acetonitrile, then further diluted with approximately 4 volumes of Et$_2$O. After 10 min, the resulting crystals were collected by vacuum filtration, washing with Et$_2$O, to afford a higher purity sample for spectra. $^1$H NMR (500 MHz, CDCl$_3$) δ 8.14 (t, J=1.7 Hz, 1H), 8.00 (d, J=0.5 Hz, 1H), 7.92-7.86 (m, 1H), 7.49-7.45 (m, 1H), 7.44-7.39 (m, 1H), 7.36-7.28 (m, 1H), 3.62-3.52 (m, 4H), 2.78-2.67 (m, 2H), 2.42 (d, J=1.1 Hz, 3H), 2.26-2.14 (m, 2H). LCMS (M+H)=476.1.

Intermediate 9

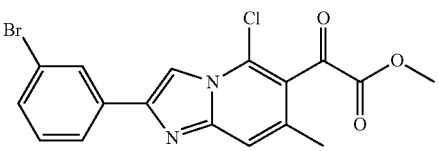

Methyl 2-(2-(3-bromophenyl)-5-chloro-7-methyl-imidazo[1,2-a]pyridin-6-yl)-2-oxoacetate A suspension of 3-[2-(3-Bromophenyl)-5-chloro-7-methylimidazo[1,2-a]pyridin-6-yl]-3-oxo-2-[(1E)-1λ$^4$-thiolan-1-ylidene]propanenitrile (18.92 g, 39.8 mmol) and oxone (39.2 g, 63.8 mmol) in anhydrous MeOH (660 ml) was heated (75° C. oil bath) and stirred exposed to air. Additional oxone (12.25 g, 19.92 mmol) was added after each of 5 hrs and 7.5 hrs respectively. The temperature was reduced (40° C.) and the reaction was stirred for 16 hrs, then warmed again (80° C.) and stirred for 20 hrs. Solids were removed by filtration, and the filtrate was concentrated. The residue was dissolved in EtOAc and washed with water. The organic layer was dried (MgSO$_4$) and concentrated to a small volume. Solids were collected and the filtrate was further concentrated, affording a second crop of solids, both of similar purity, and combined to afford the desired product (9 g, 22.08 mmol, 55.4% yield) as a yellow powdery solid. $^1$H NMR (400 MHz, CDCl$_3$) δ 8.15 (s, 1H), 8.04 (s, 1H), 7.91 (d, J=7.8 Hz, 1H), 7.52 (d, J=8.0 Hz, 1H), 7.48 (s, 1H), 7.34 (t, J=7.8 Hz, 1H), 4.01 (s, 3H), 2.42 (s, 3H); LCMS (ESI, M+1): 409.0.

Intermediate 10

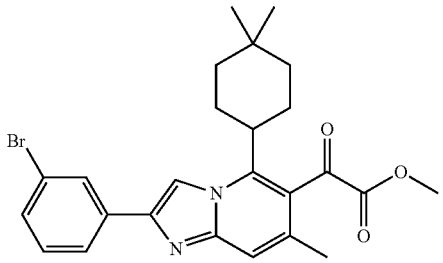

Methyl 2-(2-(3-bromophenyl)-5-(4,4-dimethylpiperidin-1-yl)-7-methylimidazo[1,2-a]pyridin-6-yl)-2-oxoacetate To a stirred solution of methyl 2-(2-(3-bromophenyl)-5-chloro-7-methylimidazo[1,2-a]pyridin-6-yl)-2-oxoacetate (1.97 g, 4.11 mmol) in DMF (20 mL) was added 4,4-dimethylpiperidine (0.558 g, 4.93 mmol) followed by DIEA (2.152 ml, 12.32 mmol) at rt. The resulting dark reaction mixture was stirred for 2 hrs and diluted with ether (150 mL), washed with water (5×25 mL), brine (25 mL), dried (MgSO$_4$), filtered, concentrated and purified by flash chromatography using 1-lit each of 10, 20 and 30% EtOAc/Hex to afford the desired product (1.66 g, 3.43 mmol, 83% yield) as a yellow solid. The desired product came out with 20-30% EtOAc/Hex. $^1$H NMR (500 MHz, CDCl$_3$) δ 8.14 (t, J=1.7 Hz, 1H), 7.91 (qd, J=0.8, 7.8 Hz, 1H), 7.85 (d, J=0.3 Hz, 1H), 7.50 (ddd, J=1.1, 2.0, 8.0 Hz, 1H), 7.32-7.37 (m, 2H), 3.99 (s, 3H), 3.52 (br. s., 2H), 2.98 (br. s., 2H), 2.37 (d, J=1.1 Hz, 3H), 1.51-1.57 (m, 4H), 1.15 (br. s., 3H), 1.08 (br. s., 3H). LCMS (M+H)=486.1.

Intermediate 11

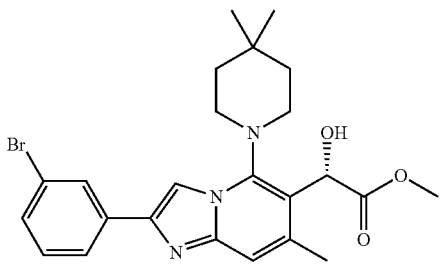

(S)-Methyl 2-(2-(3-bromophenyl)-5-(4,4-dimethylpiperidin-1-yl)-7-methylimidazo[1,2-a]pyridin-6-yl)-2-hydroxyacetate A solution of methyl 2-(2-(3-bromophenyl)-5-(4,4-dimethylpiperidin-1-yl)-7-methylimidazo[1,2-a]pyridin-6-yl)-2-oxoacetate (1.58 g, 3.26 mmol) in anhydrous toluene (30 ml) was treated with (R)-1-methyl-3,3-diphenylhexahydropyrrolo[1,2-c][1,3,2]oxazaborole (0.362 g, 1.305 mmol), the mixture was cooled (−40° C., dry ice/acetonitrile), and a solution of 50% catecholborane in toluene (1.119 ml, 4.57 mmol) was added dropwise. The reaction mixture was stirred for 30 min, then slowly warmed to −15° C. and stirred for 90 min. The mixture was diluted with EtOAc (75 mL) and saturated aqueous. Na$_2$CO$_3$ (75 mL). The mixture was stirred vigorously for 30 min, and the organic phase washed with sat Na$_2$CO$_3$ (5×75 mL), dried (MgSO$_4$), filtered and concentrated. The product was used as-is in the following step. This product is recovered partially as unreacted starting material in the following step, and the purified material was used for high quality analytical spectra. $^1$H NMR (500 MHz, CDCl$_3$) δ 8.11 (t, J=1.7 Hz, 1H), 7.88 (s, 1H), 7.88-7.83 (m, 1H), 7.46 (ddd, J=8.0, 2.0, 0.9 Hz, 1H), 7.33 (s, 1H), 7.33-7.28 (m, 1H), 5.62 (d, J=5.2 Hz, 1H), 4.44 (d, J=4.7 Hz, 1H), 3.79 (s, 3H), 3.65-3.53 (m, 2H), 3.02 (dt, J=11.9, 4.0 Hz, 1H), 2.90 (dt, J=11.6, 4.0 Hz, 1H), 2.41 (d, J=0.9 Hz, 3H), 1.77-1.66 (m, 2H), 1.58-1.47 (m, 2H), 1.17 (s, 3H), 1.09 (s, 3H). $^{13}$C NMR (126 MHz, CDCl$_3$) δ 174.3, 146.8, 143.7, 142.2, 136.8, 135.9, 130.8, 130.2, 129.0, 124.6, 122.9, 120.6, 115.8, 106.6, 68.2, 52.9, 45.3, 44.6, 38.5, 38.4, 30.6, 28.3, 25.6, 20.1. LCMS (M+H)=488.1.

Intermediate 12

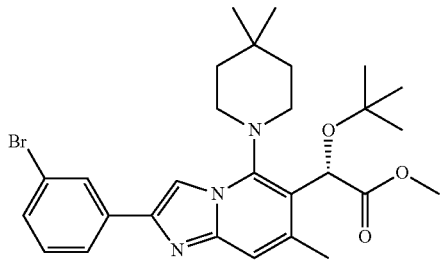

(S)-Methyl 2-(2-(3-bromophenyl)-5-(4,4-dimethylpiperidin-1-yl)-7-methylimidazo[1,2-a]pyridin-6-yl)-2-(tert-butoxy)acetate A solution of (S)-methyl 2-(2-(3-bromophenyl)-5-(4,4-dimethylpiperidin-1-yl)-7-methylimidazo[1,2-a]pyridin-6-yl)-2-hydroxyacetate (1.050 g, 2.159 mmol) in CH$_2$Cl$_2$ (100 mL) was treated with 70% aq. HClO$_4$ (0.204 mL, 2.375 mmol), cooled (0° C. ice bath), then sparged with isobutylene gas for 5 min. The reaction was sealed, stirred with cooling for 30 min, then allowed to warm to room temperature with stirring over 16 hrs. The reaction was quenched with saturated aqueous Na$_2$CO$_3$ (50 mL) and stirred for 10 min. The layers were separated and the organic layer was dried (MgSO$_4$), filtered, and concentrated under reduced pressure. The residue was purified by biotage (80 g SiO$_2$, 10% (3 CV), 0-60% (15 CV), 60% (2 CV), EtOAc in hexanes). Product fractions were pooled and concentrated under reduced pressure, affording the product (1.05 g, 1.935 mmol, 90% yield) as a white glassy solid after drying twice from Et$_2$O. $^1$H NMR (500 MHz, CDCl$_3$) δ 8.11 (t, J=1.7 Hz, 1H), 7.88 (dt, J=8.0, 1.2 Hz, 1H), 7.86 (s, 1H), 7.47-7.43 (m, 1H), 7.31 (t, J=7.9 Hz, 1H), 7.29 (s, 1H), 6.05 (s, 1H), 3.70 (s, 3H), 3.70-3.63 (m, 1H), 3.55 (td, J=11.6, 2.6 Hz, 1H), 3.17-3.09 (m, 1H), 2.97-2.90 (m, 1H), 2.46 (d, J=0.9 Hz, 3H), 1.76-1.64 (m, 2H), 1.57-1.46 (m, 2H), 1.26 (s, 9H), 1.19 (s, 3H), 1.10 (s, 3H). $^{13}$C NMR (126 MHz, CDCl$_3$) δ 173.3, 147.0, 143.6, 141.0, 137.9, 136.3, 130.7, 130.2, 128.9, 124.6, 122.9, 122.2, 115.9, 106.7, 75.8, 69.1, 52.3, 45.3, 44.0, 39.3, 38.7, 32.0, 28.5, 28.1, 24.7, 20.7. LCMS (M+H)=544.2.

Intermediate 13

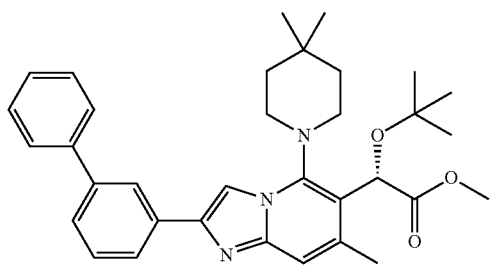

(S)-Methyl 2-(2-([1,1'-biphenyl]-3-yl)-5-(4,4-dimethylpiperidin-1-yl)-7-methylimidazo[1,2-a]pyridin-6-yl)-2-(tert-butoxy)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.0515 g, 0.095 mmol), phenylboronic acid (0.023 g, 0.190 mmol) and 2.0 M aq. Na$_2$CO$_3$ (0.142 ml, 0.285 mmol) in DMF (1.0 ml) was sparged with nitrogen for 5 min, then treated with Pd(Ph$_3$P)$_4$ (7.68 mg, 6.65 µmol), and sparged for an additional 2 minutes. The flask was sealed and heated (85° C. oil bath) for 2 hrs. The reaction was cooled, diluted with water (3 mL), treated with 1.0N HCl (1 mL), and extracted with Et$_2$O (2×10 mL). The combined organic extracts were concentrated and the residue was purified by biotage (12 g SiO$_2$, 0% (3 CV), 0-60% (15 CV), 60% (2 CV), EtOAc in hexanes). Product fractions were pooled and concentrated under reduced pressure, affording the product (0.030 g, 0.056 mmol, 58.6% yield) as a clear film. $^1$H NMR (500 MHz, CDCl$_3$) δ 8.19 (t, J=1.7 Hz, 1H), 7.94-7.90 (m, 2H), 7.73-7.68 (m, 2H), 7.59-7.55 (m, 1H), 7.54-7.50 (m, 1H), 7.50-7.45 (m, 2H), 7.41-7.36 (m, 1H), 7.32 (s, 1H), 6.08 (s, 1H), 3.75-3.66 (m, 4H), 3.58 (td, J=11.7, 2.5 Hz, 1H), 3.17-3.10 (m, 1H), 2.98-2.90 (m, 1H), 2.46 (d, J=0.8 Hz, 3H), 1.77-1.65 (m, 2H), 1.58-1.46 (m, 2H), 1.26 (s, 9H), 1.18 (s, 3H), 1.10 (s, 3H). $^{13}$C NMR (126 MHz, CDCl$_3$) δ 173.4, 147.0, 145.1, 141.7, 141.2, 141.0, 137.5, 134.6, 129.0, 128.7, 127.3, 127.3, 126.7, 125.1, 124.9, 121.9, 115.9, 106.5, 75.7, 69.1, 52.2, 45.2, 43.9, 39.2, 38.7, 32.1, 28.5, 28.1, 24.6, 20.6. LCMS (M+H)=540.4.

Example 1

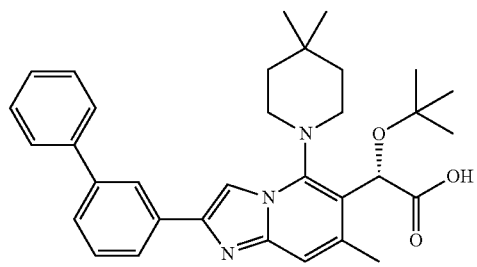 [SMILES: Cc1cc2nc(-c3cccc(-c4ccccc4)c3)cn2c(N2CCC(C)(C)CC2)c1[C@H](OC(C)(C)C)C(=O)O]

(S)-2-(2-([1,1'-Biphenyl]-3-yl)-5-(4,4-dimethylpiperidin-1-yl)-7-methylimidazo[1,2-a]pyridin-6-yl)-2-(tert-butoxy)acetic Acid A solution of (S)-methyl 2-(2-([1,1'-biphenyl]-3-yl)-5-(4,4-dimethylpiperidin-1-yl)-7-methylimidazo[1,2-a]pyridin-6-yl)-2-(tert-butoxy)acetate (0.030 g, 0.056 mmol) in MeOH (0.5 mL) and THF (0.5 mL) was treated with 1.0 M aq. LiOH (0.30 mL, 0.300 mmol) and the mixture was heated (85° C. heating block) for 2 hrs. The reaction was cooled, filtered (0.45 m syringe tip filter) and purified by preparative-HPLC. Product fractions were pooled, concentrated and the remaining aqueous layer was extracted with EtOAc (3×15 mL). The combined organic layers were dried (MgSO$_4$), filtered and concentrated under reduced pressure, affording the product (0.022 g, 0.042 mmol, 74.9% yield) as a white powder after drying once from Et$_2$O. $^1$H NMR (500 MHz, CDCl$_3$) δ 8.16 (t, J=1.6 Hz, 1H), 7.91 (s, 1H), 7.89 (dt, J=7.6, 1.3 Hz, 1H), 7.72-7.68 (m, 2H), 7.60-7.55 (m, 1H), 7.54-7.49 (m, 1H), 7.47 (t, J=7.6 Hz, 2H), 7.40-7.35 (m, 2H), 6.01 (br. s., 1H), 3.77-3.68 (m, 1H), 3.59 (td, J=11.9, 2.3 Hz, 1H), 3.31 (d, J=11.0 Hz, 1H), 2.89 (d, J=11.5 Hz, 1H), 2.49 (s, 3H), 1.75-1.60 (m, 2H), 1.53 (d, J=12.8 Hz, 1H), 1.49-1.41 (m, 1H), 1.30 (s, 9H), 1.16 (s, 3H), 1.07 (s, 3H). $^{13}$C NMR (126 MHz, CDCl$_3$) δ 172.5, 147.0, 145.1, 142.0, 141.8, 141.1, 134.2, 129.1, 128.7, 127.4, 127.3, 126.9, 125.2, 125.1, 115.9, 106.7, 69.2, 45.8, 43.8, 38.7, 32.5, 28.4, 28.3, 24.2, 20.7. LCMS (M+H)=526.4.

Intermediate 14

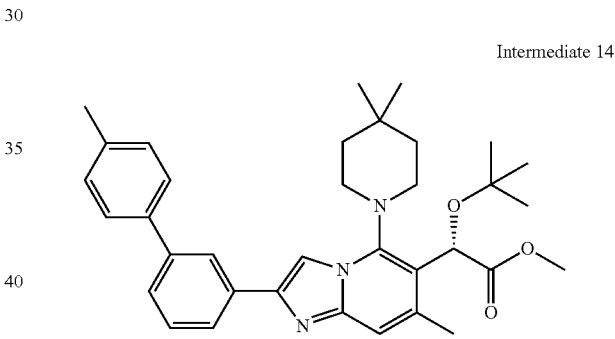

(S)-Methyl 2-(tert-butoxy)-2-(5-(4,4-dimethylpiperidin-1-yl)-7-methyl-2-(4'-methyl-[1,1'-biphenyl]-3-yl)imidazo[1,2-a]pyridin-6-yl)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.0514 g, 0.095 mmol), p-tolylboronic acid (0.026 g, 0.189 mmol) and 2.0 M aq. Na$_2$CO$_3$ (0.142 ml, 0.284 mmol) in DMF (1.0 ml) was sparged with nitrogen for 5 min, then treated with Pd(Ph$_3$P)$_4$ (7.66 mg, 6.63 µmol), and sparged for an additional 2 minutes. The flask was sealed and heated (85° C. heating block) for 2 hrs, then cooled. The reaction was diluted with water (3 mL), treated with 1.0N HCl (1 mL), and extracted with Et$_2$O (2×10 mL). The combined organic extracts were concentrated and the residue was purified by biotage (12 g SiO2, 0% (3 CV), 0-60% (15 CV), 60% (2 CV), EtOAc in hexanes). Product fractions were pooled and concentrated under reduced pressure, affording the product (0.047 g, 0.085 mmol, 90% yield) as a clear film. 1H NMR (500 MHz, CDCl$_3$) δ 8.17 (t, J=1.6 Hz, 1H), 7.91 (s, 1H), 7.89 (dt, J=7.5, 1.4 Hz, 1H), 7.63-7.59 (m, 2H), 7.57-7.53 (m, 1H), 7.52-7.48 (m, 1H), 7.33-7.27 (m, 3H), 6.08 (s, 1H), 3.75-

3.66 (m, 4H), 3.61-3.53 (m, 1H), 3.18-3.09 (m, 1H), 2.98-2.89 (m, 1H), 2.46 (d, J=0.9 Hz, 3H), 2.42 (s, 3H), 1.77-1.65 (m, 2H), 1.57-1.46 (m, 2H), 1.26 (s, 9H), 1.18 (s, 3H), 1.10 (s, 3H). $^{13}$C NMR (126 MHz, CDCl$_3$) δ 173.4, 146.9, 145.1, 141.7, 141.0, 138.3, 137.6, 137.1, 134.5, 129.4, 129.0, 127.2, 126.6, 124.9, 124.8, 122.0, 115.9, 106.6, 75.8, 69.1, 52.3, 45.2, 43.9, 39.3, 38.8, 32.1, 28.5, 28.2, 24.6, 21.2, 20.7. LCMS (M+H)=554.3.

Example 2

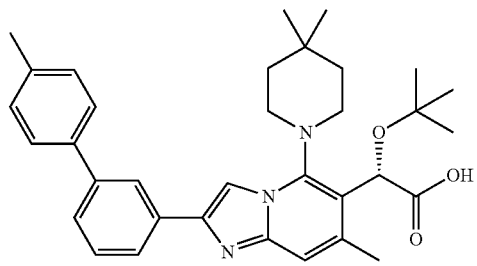 [SMILES: Cc1ccc(-c2cccc(-c3cn4c(N5CCC(C)(C)CC5)c([C@H](OC(C)(C)C)C(=O)O)c(C)cc4n3)c2)cc1]

(S)-2-(tert-butoxy)-2-(5-(4,4-dimethylpiperidin-1-yl)-7-methyl-2-(4'-methyl-[1,1'-biphenyl]-3-yl)imidazo[1,2-a]pyridin-6-yl)acetic Acid A solution of (S)-methyl 2-(tert-butoxy)-2-(5-(4,4-dimethylpiperidin-1-yl)-7-methyl-2-(4'-methyl-[1,1'-biphenyl]-3-yl)imidazo[1,2-a]pyridin-6-yl)acetate (0.047 g, 0.085 mmol) in EtOH (2 mL) was treated with lithium hydroxide monohydrate (0.019 g, 0.453 mmol) and heated (85° C. heating block) and stirred for 1 hr. The reaction was treated with MeOH (1 mL) and heated for 3.5 hrs, then cooled, filtered (0.45 µm syringe tip filter) and the filtrate was purified by preparative LCMS. Product fractions were combined and dried via centrifugal evaporation, to afford the product (0.0381 g, 0.071 mmol, 83% yield) as an off-white solid. $^1$H NMR (500 MHz, DMSO-d$_6$) δ 8.29 (d, J=7.0 Hz, 2H), 8.05 (d, J=7.7 Hz, 1H), 7.64 (d, J=8.1 Hz, 2H), 7.60-7.55 (m, 1H), 7.52-7.47 (m, 1H), 7.31 (d, J=8.1 Hz, 2H), 7.28 (s, 1H), 5.93 (br. s., 1H), 3.77 (t, J=11.2 Hz, 1H), 3.56 (t, J=11.6 Hz, 1H), 3.10 (d, J=11.0 Hz, 1H), 2.84 (d, J=11.7 Hz, 1H), 2.39 (s, 3H), 2.36 (s, 3H), 1.72-1.57 (m, 2H), 1.55-1.39 (m, 2H), 1.19 (s, 12H), 1.04 (s, 3H). LCMS (M+H)=540.4.

Intermediate 15

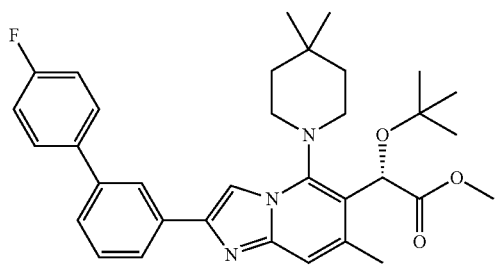

(S)-Methyl 2-(tert-butoxy)-2-(5-(4,4-dimethylpiperidin-1-yl)-2-(4'-fluoro-[1,1'-biphenyl]-3-yl)-7-methylimidazo[1,2-a]pyridin-6-yl)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.0512 g, 0.094 mmol), (4-fluorophenyl)boronic acid (0.026 g, 0.189 mmol) and 2.0 M aq. Na$_2$CO$_3$ (0.142 ml, 0.283 mmol) in DMF (1.0 ml) was sparged with nitrogen for 5 min, then treated with Pd(Ph$_3$P)$_4$ (7.63 mg, 6.61 µmol), and sparged for 2 minutes. The flask was sealed and heated (85° C. heating block) for 2 hrs, then cooled. The reaction was diluted with water (3 mL), treated with 1.0 N HCl (1 mL), and extracted with Et$_2$O (2×10 mL). The combined organic extracts were dried (MgSO$_4$), concentrated and the residue was purified by biotage (12 g SiO$_2$, 0% (3 CV), 0-60% (15 CV), 60% (2 CV), EtOAc in hexanes). Product fractions were pooled and concentrated under reduced pressure, affording the product (0.0273 g, 0.049 mmol, 51.9% yield) as a clear film. $^1$H NMR (500 MHz, CDCl$_3$) δ 8.18-8.15 (m, 1H), 7.92 (s, 1H), 7.91-7.86 (m, 1H), 7.70-7.64 (m, 2H), 7.53-7.50 (m, 2H), 7.32 (s, 1H), 7.19-7.13 (m, 2H), 6.07 (s, 1H), 3.73-3.66 (m, 4H), 3.58 (td, J=11.7, 2.5 Hz, 1H), 3.14 (dt, J=11.9, 3.3 Hz, 1H), 2.98-2.90 (m, 1H), 2.46 (d, J=0.8 Hz, 3H), 1.77-1.65 (m, 2H), 1.58-1.46 (m, 2H), 1.26 (s, 9H), 1.18 (s, 3H), 1.10 (s, 3H). $^{13}$C NMR (126 MHz, CDCl$_3$) δ 173.4, 163.5, 161.6, 147.0, 145.0, 141.0, 140.8, 137.6, 137.3, 137.3, 134.7, 129.1, 129.0, 128.9, 126.5, 125.0, 124.8, 122.0, 115.9, 115.6, 115.5, 106.6, 75.8, 69.1, 52.3, 45.2, 43.9, 39.3, 38.7, 32.1, 28.5, 28.1, 24.6, 20.7. LCMS (M+H)=558.3.

Example 3

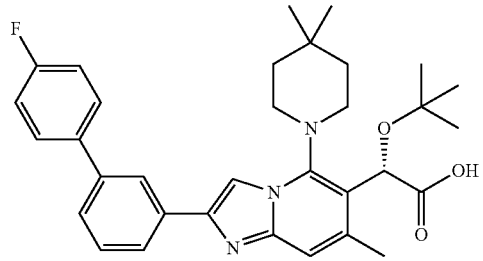

(S)-2-(tert-Butoxy)-2-(5-(4,4-dimethylpiperidin-1-yl)-2-(4'-fluoro-[1,1'-biphenyl]-3-yl)-7-methylimidazo[1,2-a]pyridin-6-yl)acetic Acid A solution of (S)-methyl 2-(tert-butoxy)-2-(5-(4,4-dimethylpiperidin-1-yl)-2-(4'-fluoro-[1,1'-biphenyl]-3-yl)-7-methylimidazo[1,2-a]pyridin-6-yl)acetate (0.032 g, 0.057 mmol) in MeOH (1.5 mL) was treated with lithium hydroxide monohydrate (0.0162 g, 0.386 mmol) and heated (85° C. heating block) for 2 hrs, cooled, and filtered (0.45 µm syringe tip filter). The filtrate was purified by preparative LCMS, and product fractions were combined and dried via centrifugal evaporation, to afford the desired product (0.0283 g, 0.052 mmol, 91% yield) as an off-white solid. $^1$H NMR (500 MHz, CD$_3$OD) δ 8.20 (t, J=1.6 Hz, 1H), 8.15 (s, 1H), 7.91 (dt, J=7.7, 1.3 Hz, 1H), 7.79-7.71 (m, 2H), 7.63-7.58 (m, 1H), 7.56-7.50 (m, 1H), 7.26 (s, 1H), 7.24-7.17 (m, 2H), 5.99 (s, 1H), 3.84-3.73 (m, 1H), 3.66-3.56 (m, 1H), 3.44-3.36 (m, 1H), 3.03 (d, J=12.0 Hz, 1H), 2.53 (d, J=0.6 Hz, 3H), 1.83-1.70 (m, 2H), 1.59 (d, J=13.2 Hz, 1H), 1.51 (d, J=12.9 Hz, 1H), 1.26 (s, 9H), 1.21 (s, 3H), 1.10 (s, 3H). $^{13}$C NMR (101 MHz, CD$_3$OD) δ 175.7, 163.9, 161.4, 145.8, 145.8, 142.7, 142.6, 141.3, 141.3, 140.7, 140.7, 137.1, 137.1, 133.0, 129.1, 128.6, 128.5, 126.5, 124.8, 124.5, 124.3, 115.3, 115.1, 113.0, 107.1, 75.4, 69.5, 45.4, 43.9, 43.7, 39.1, 38.6, 30.8, 28.1, 27.2, 23.9, 19.8. LCMS (M+H)=544.3.

Intermediate 16

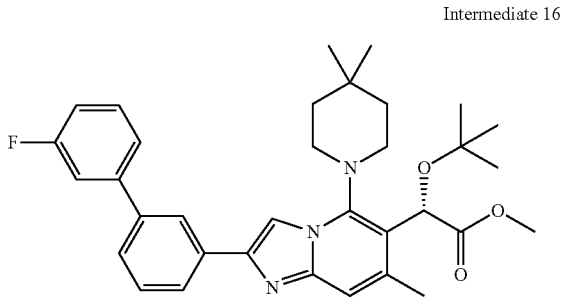 [SMILES: COC(=O)[C@@H](OC(C)(C)C)c1c(C)cc2nc(-c3cccc(-c4cccc(F)c4)c3)cn2c1N1CCC(C)(C)CC1]

(S)-Methyl 2-(tert-butoxy)-2-(5-(4,4-dimethylpiperidin-1-yl)-2-(3'-fluoro-[1,1'-biphenyl]-3-yl)-7-methylimidazo[1,2-a]pyridin-6-yl)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.0532 g, 0.098 mmol), (3-fluorophenyl)boronic acid (0.032 g, 0.229 mmol) and 2.0 M aq. Na₂CO₃ (0.150 ml, 0.300 mmol) in DMF (1.0 ml) was sparged with nitrogen for 5 min, then treated with Pd(Ph₃P)₄ (0.0102 g, 8.83 μmol), and sparged for an additional 2 minutes. The flask was sealed and heated (85° C. heating block) for 2 hrs, then the reaction was cooled, diluted with water (3 mL), treated with 1.0N HCl (1 mL), and extracted with Et₂O (2×10 mL). The combined organic extracts were concentrated and the residue was purified by biotage (12 g SiO₂, 0% (3 CV), 0-60% (15 CV), 60% (2 CV), EtOAc in hexanes). Product fractions were pooled and concentrated under reduced pressure, affording the product (0.037 g, 0.066 mmol, 67.7% yield) as a clear film. ¹H NMR (500 MHz, CDCl₃) δ 8.21-8.17 (m, 1H), 7.95-7.88 (m, 2H), 7.55-7.52 (m, 2H), 7.50-7.47 (m, 1H), 7.46-7.38 (m, 2H), 7.32 (s, 1H), 7.10-7.03 (m, 1H), 6.07 (s, 1H), 3.76-3.67 (m, 4H), 3.58 (td, J=11.6, 2.5 Hz, 1H), 3.19-3.10 (m, 1H), 2.95 (d, J=11.8 Hz, 1H), 2.47 (d, J=0.9 Hz, 3H), 1.78-1.65 (m, 2H), 1.55-1.46 (m, 2H), 1.28-1.25 (m, 9H), 1.19 (s, 3H), 1.10 (s, 3H). ¹³C NMR (126 MHz, CDCl₃) δ 173.3, 164.1, 162.2, 147.0, 144.8, 143.5, 143.4, 141.0, 140.5, 140.5, 137.6, 134.8, 130.1, 130.1, 129.1, 126.5, 125.6, 124.8, 123.0, 123.0, 122.0, 115.9, 114.3, 114.1, 114.1, 114.0, 106.5, 75.8, 69.1, 52.2, 45.2, 43.9, 39.2, 38.7, 32.0, 28.5, 28.1, 24.6, 20.6. LCMS (M+H)=558.3.

Example 4

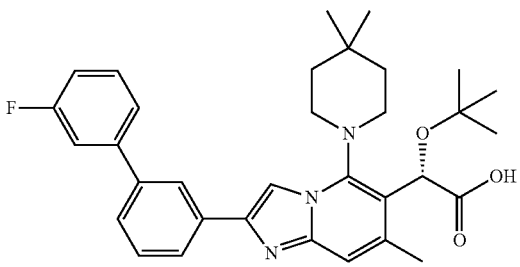 [SMILES: Cc1cc2nc(-c3cccc(-c4cccc(F)c4)c3)cn2c(N2CCC(C)(C)CC2)c1[C@H](OC(C)(C)C)C(=O)O]

(S)-2-(tert-butoxy)-2-(5-(4,4-dimethylpiperidin-1-yl)-2-(3'-fluoro-[1,1'-biphenyl]-3-yl)-7-methylimidazo[1,2-a]pyridin-6-yl)acetic Acid A solution of (S)-methyl 2-(tert-butoxy)-2-(5-(4,4-dimethylpiperidin-1-yl)-2-(3'-fluoro-[1,1'-biphenyl]-3-yl)-7-methylimidazo[1,2-a]pyridin-6-yl)acetate (0.037 g, 0.066 mmol) in MeOH (1.5 mL) was treated with lithium hydroxide monohydrate (0.021 g, 0.500 mmol) and heated (85° C. heating block) for 2 hrs. The reaction was cooled, filtered (0.45 μm syringe tip filter), and purified by preparative LCMS. Product fractions were combined and dried via centrifugal evaporation, to afford the desired product (0.0394 g, 0.069 mmol, 70.3% yield) as an off-white solid. ¹H NMR (500 MHz, CD₃OD) δ 9.11 (t, J=1.7 Hz, 1H), 9.04 (s, 1H), 8.93-8.87 (m, 1H), 8.45-8.29 (m, 5H), 8.07-8.01 (m, 1H), 7.92 (s, 1H), 6.33 (br. s., 1H), 4.48 (br, 2H), 4.33-4.21 (m, 2H), 2.62 (s, 3H), 2.48-2.28 (m, 3H), 2.20 (d, J=10.7 Hz, 1H), 1.99 (s, 3H), 1.95 (s, 9H), 1.84 (s, 3H). ¹³C NMR (101 MHz, CD₃OD) δ 183.5, 182.5, 173.5, 171.1, 155.5, 152.6, 152.5, 152.4, 149.4, 148.8, 148.7, 148.1, 144.7, 140.5, 140.4, 138.8, 135.5, 135.2, 134.7, 133.5, 132.6, 132.6, 123.9, 123.7, 123.3, 123.0, 116.6, 83.7, 80.5, 54.7, 53.2, 38.1, 37.7, 32.1, 30.3. LCMS (M+H)=544.3.

Intermediate 17

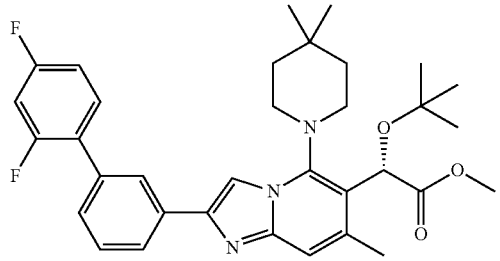

(S)-Methyl 2-(tert-butoxy)-2-(2-(2',4'-difluoro-[1,1'-biphenyl]-3-yl)-5-(4,4-dimethylpiperidin-1-yl)-7-methylimidazo[1,2-a]pyridin-6-yl)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.0532 g, 0.098 mmol), (2,4-difluorophenyl)boronic acid (0.031 g, 0.196 mmol) and 2.0 M aq. Na₂CO₃ (0.147 ml, 0.294 mmol) in DMF (1.5 ml) was sparged with nitrogen for 5 min, then treated with Pd(Ph₃P)₄ (7.93 mg, 6.86 μmol), and sparged for an additional 2 minutes. The flask was sealed and heated (85° C. heating block) for 2 hrs, then cooled, diluted with water (3 mL), treated with 1.0N HCl (1 mL), and extracted with Et₂O (2×10 mL). The combined organic extracts were concentrated and the residue was purified by biotage (12 g SiO₂, 0% (3 CV), 0-60% (15 CV), 60% (2 CV), EtOAc in hexanes). Product fractions were pooled and concentrated under reduced pressure, affording the product which was then used immediately in the following step. LCMS (M+H)=576.3.

Example 5

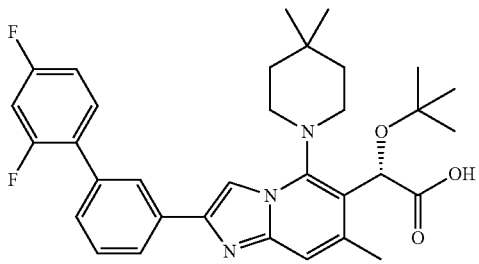 [SMILES: Cc1ccc(-c2cccc(-c3cn4c(N5CCC(C)(C)CC5)c([C@H](OC(C)(C)C)C(=O)O)c(C)cc4n3)c2)c(F)c1]

(S)-2-(tert-Butoxy)-2-(2-(2',4'-difluoro-[1,1'-biphenyl]-3-yl)-5-(4,4-dimethylpiperidin-1-yl)-7-methylimidazo[1,2-a]pyridin-6-yl)acetic Acid A solution of(S)-methyl 2-(tert-butoxy)-2-(2-(2',4'-difluoro-[1,1'-biphenyl]-3-yl)-5-(4,4-dimethylpiperidin-1-yl)-7-methylimidazo[1,2-a]pyridin-6-yl)acetate (0.056 g, 0.098 mmol) in MeOH (1.5 mL) was treated with lithium hydroxide monohydrate (0.032 g, 0.763 mmol) and heated (85° C. heating block) for 2 hrs. The reaction was cooled then filtered (0.45 μm syringe tip filter), and purified by preparative LCMS. Product fractions were combined and dried via centrifugal evaporation, to afford (0.0376 g, 0.067 mmol, 68.3% yield) as a light gray solid. $^1$H NMR (500 MHz, CD$_3$OD) δ 8.15-8.06 (m, 2H), 7.95 (dt, J=7.6, 1.5 Hz, 1H), 7.66-7.58 (m, 1H), 7.56-7.46 (m, 2H), 7.20 (s, 1H), 7.13-7.03 (m, 2H), 5.88 (s, 1H), 3.78-3.70 (m, 1H), 3.63-3.55 (m, 1H), 3.54-3.49 (m, 1H), 3.10-3.00 (m, 1H), 2.53 (d, J=0.9 Hz, 3H), 1.80-1.69 (m, 2H), 1.58 (d, J=12.9 Hz, 1H), 1.50 (d, J=12.9 Hz, 1H), 1.25 (s, 9H), 1.19 (s, 3H), 1.09 (s, 3H). $^{13}$C NMR (101 MHz, CD$_3$OD) δ 178.7, 177.4, 165.3, 165.2, 162.9, 162.7, 162.6, 162.5, 160.2, 160.0, 147.9, 147.8, 144.5, 144.4, 142.4, 142.3, 142.0, 137.0, 135.1, 133.3, 133.2, 133.2, 133.1, 130.2, 129.8, 129.8, 127.7, 127.7, 126.7, 114.6, 113.0, 112.9, 112.8, 112.7, 108.4, 105.6, 105.3, 105.0, 76.5, 71.8, 46.9, 45.4, 45.3, 40.7, 40.3, 32.2, 29.6, 28.8, 25.6, 22.3, 21.4. LCMS (M+H)=562.3.

Intermediate 18

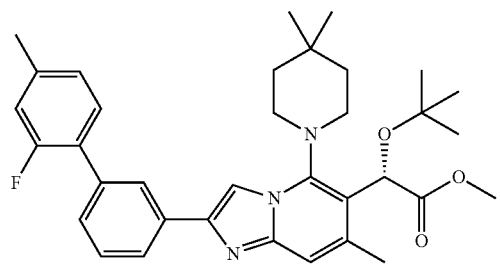

(S)-Methyl 2-(tert-butoxy)-2-(5-(4,4-dimethylpiperidin-1-yl)-2-(2'-fluoro-4'-methyl-[1,1'-biphenyl]-3-yl)-7-methylimidazo[1,2-a]pyridin-6-yl)acetate A solution of(S)-methyl 2-(2-(3-bromophenyl)-5-(4,4-dimethylpiperidin-1-yl)-7-methylimidazo[1,2-a]pyridin-6-yl)-2-(tert-butoxy)acetate (0.0532 g, 0.098 mmol), (2-fluoro-4-methylphenyl)boronic acid (0.030 g, 0.196 mmol) and 2.0 M aq. Na$_2$CO$_3$ (0.147 ml, 0.294 mmol) in DMF (1.0 ml) was sparged with nitrogen for 5 min, then treated with Pd(Ph$_3$P)$_4$ (7.93 mg, 6.86 μmol), and sparged for an additional 2 minutes. The flask was sealed and heated (85° C. heating block) for 2 hrs, then cooled. The reaction was diluted with water (3 mL), treated with 1.0N HCl (1 mL), and extracted with Et$_2$O (2×10 mL). The combined organic extracts were concentrated and the residue was purified by biotage (12 g SiO$_2$, 0% (3 CV), 0-60% (15 CV), 60% (2 CV), EtOAc in hexanes). Product fractions were pooled and concentrated under reduced pressure, affording as a yellow film. LCMS (M+H)=572.3.

Example 6

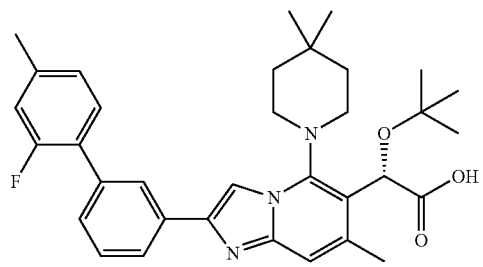

(S)-2-(tert-Butoxy)-2-(5-(4,4-dimethylpiperidin-1-yl)-2-(2'-fluoro-4'-methyl-[1,1'-biphenyl]-3-yl)-7-methylimidazo[1,2-a]pyridin-6-yl)acetic Acid A solution of (S)-methyl 2-(tert-butoxy)-2-(5-(4,4-dimethylpiperidin-1-yl)-2-(2'-fluoro-4'-methyl-[1,1'-biphenyl]-3-yl)-7-methylimidazo[1,2-a]pyridin-6-yl)acetate (0.056 g, 0.098 mmol) in MeOH (1.5 mL) was treated with lithium hydroxide monohydrate (0.036 g, 0.858 mmol) and heated (85° C. heating block) for 2 hrs, cooled, and filtered (0.45 μm syringe tip filter). The filtrate was purified by preparative LCMS, and product fractions were combined and dried via centrifugal evaporation, to afford the desired product (0.0463 g, 0.083 mmol, 85% yield) as an off white solid. $^1$H NMR (500 MHz, DMSO-d$_6$) δ 8.26 (s, 1H), 8.18 (s, 1H), 8.08 (d, J=7.7 Hz, 1H), 7.56-7.41 (m, 3H), 7.26 (s, 1H), 7.20-7.10 (m, 2H), 5.91 (br. s., 1H), 3.74 (t, J=10.5 Hz, 1H), 3.53 (t, J=10.6 Hz, 1H), 3.11 (d, J=11.0 Hz, 1H), 2.83 (d, J=11.4 Hz, 1H), 2.38 (d, J=4.4 Hz, 6H), 1.70-1.55 (m, 2H), 1.50 (d, J=12.5 Hz, 1H), 1.43 (d, J=13.6 Hz, 1H), 1.25-1.11 (m, 12H), 1.03 (s, 3H). LCMS (M+H)=558.4.

Intermediate 19

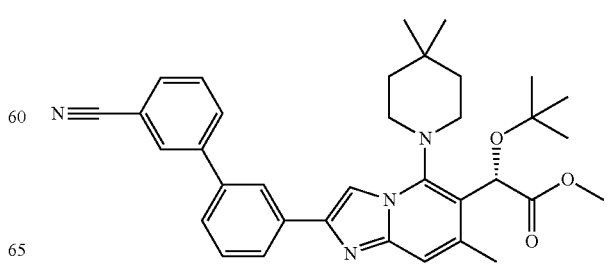

(S)-Methyl 2-(tert-butoxy)-2-(2-(3'-cyano-[1,1'-biphenyl]-3-yl)-5-(4,4-dimethylpiperidin-1-yl)-7-methylimidazo[1,2-a]pyridin-6-yl)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.0532 g, 0.098 mmol), (3-cyanophenyl)boronic acid (0.029 g, 0.196 mmol) and 2.0 M aq. $Na_2CO_3$ (0.147 ml, 0.294 mmol) in DMF (1.0 ml) was sparged with nitrogen for 5 min, then treated with $Pd(Ph_3P)_4$ (7.93 mg, 6.86 μmol), and sparged for an additional 2 minutes. The flask was sealed and heated (85° C. heating block) for 2 hrs, then cooled, diluted with water (3 mL), treated with 1.0N HCl (1 mL), and extracted with $Et_2O$ (2×10 mL). The combined organic extracts were concentrated and the residue was purified by biotage (12 g $SiO_2$, 0% (3 CV), 0-60% (15 CV), 60% (2 CV), EtOAc in hexanes). Product fractions were pooled and concentrated under reduced pressure, affording the product (0.033 g, 0.058 mmol, 59.6% yield). $^1H$ NMR (500 MHz, $CDCl_3$) δ 8.21 (t, J=1.4 Hz, 1H), 7.99 (t, J=1.5 Hz, 1H), 7.95 (t, J=1.5 Hz, 1H), 7.93 (s, 2H), 7.66 (dt, J=7.7, 1.3 Hz, 1H), 7.60-7.50 (m, 3H), 7.32 (s, 1H), 6.07 (s, 1H), 3.74-3.66 (m, 4H), 3.58 (td, J=11.7, 2.4 Hz, 1H), 3.15 (dt, J=11.9, 3.4 Hz, 1H), 2.95 (dt, J=11.7, 3.3 Hz, 1H), 2.47 (d, J=0.9 Hz, 3H), 1.79-1.66 (m, 2H), 1.59-1.46 (m, 2H), 1.26 (s, 9H), 1.19 (s, 3H), 1.10 (s, 3H). $^{13}C$ NMR (126 MHz, $CDCl_3$) δ 173.4, 147.0, 144.5, 142.4, 141.1, 139.5, 137.8, 135.1, 131.7, 130.9, 130.8, 129.5, 129.4, 126.5, 126.0, 124.8, 122.1, 118.9, 115.9, 112.9, 106.7, 75.8, 69.1, 52.3, 45.3, 43.9, 39.2, 38.7, 32.0, 28.5, 28.1, 24.6, 20.7. LCMS (M+H)=565.3.

Example 7

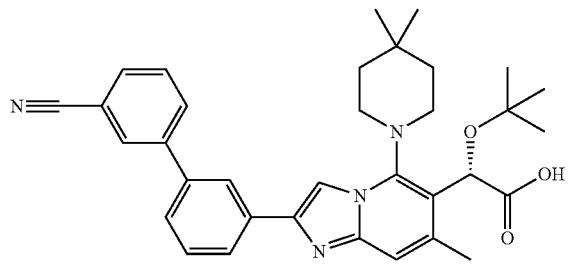 [SMILES: Cc1cc2nc(-c3cccc(-c4cccc(C#N)c4)c3)cn2c(N2CCC(C)(C)CC2)c1[C@H](OC(C)(C)C)C(=O)O]

(S)-2-(tert-Butoxy)-2-(2-(3'-cyano-[1,1'-biphenyl]-3-yl)-5-(4,4-dimethylpiperidin-1-yl)-7-methylimidazo[1,2-a]pyridin-6-yl)acetic Acid A solution of (S)-methyl 2-(tert-butoxy)-2-(2-(3'-cyano-[1,1'-biphenyl]-3-yl)-5-(4,4-dimethylpiperidin-1-yl)-7-methylimidazo[1,2-a]pyridin-6-yl)acetate (0.033 g, 0.058 mmol) in MeOH (1.5 mL) was treated with lithium hydroxide monohydrate (0.012 g, 0.292 mmol) and heated (85° C. heating block) for 2 hrs. The reaction was cooled then filtered (0.45 m syringe tip filter), and purified by preparative LCMS. Product fractions were combined and dried via centrifugal evaporation, to afford the desired product (0.0192 g, 0.033 mmol, 57.3% yield) as a light gray solid. $^1H$ NMR (500 MHz, $CD_3OD$) δ 8.27 (t, J=1.7 Hz, 1H), 8.17 (s, 1H), 8.11 (t, J=1.5 Hz, 1H), 8.08-8.03 (m, 1H), 7.98 (dt, J=7.8, 1.2 Hz, 1H), 7.74 (dt, J=7.8, 1.3 Hz, 1H), 7.70-7.64 (m, 2H), 7.61-7.55 (m, 1H), 7.25 (s, 1H), 5.98 (s, 1H), 3.84-3.75 (m, 1H), 3.61 (td, J=11.4, 2.3 Hz, 1H), 3.46-3.37 (m, 1H), 3.02 (d, J=11.8 Hz, 1H), 2.53 (d, J=0.8 Hz, 3H), 1.76 (qd, J=12.1, 4.4 Hz, 2H), 1.58 (d, J=12.6 Hz, 1H), 1.51 (d, J=13.1 Hz, 1H), 1.26 (s, 9H), 1.21 (s, 3H), 1.09 (s, 3H). $^{13}C$ NMR (101 MHz, $CD_3OD$) δ 177.5, 147.7, 147.6, 144.3, 144.2, 143.7, 142.7, 142.0, 140.9, 135.2, 132.9, 132.2, 131.8, 131.3, 130.9, 128.0, 127.3, 126.0, 126.0, 119.9, 114.7, 114.2, 108.8, 76.9, 71.1, 46.9, 45.4, 40.6, 40.2, 32.5, 29.7, 28.7, 25.3, 21.3. LCMS (M+H)=551.4.

Intermediate 20

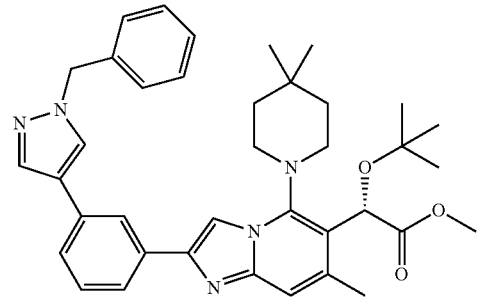

(S)-Methyl 2-(2-(3-(1-benzyl-1H-pyrazol-4-yl)phenyl)-5-(4,4-dimethylpiperidin-1-yl)-7-methylimidazo[1,2-a]pyridin-6-yl)-2-(tert-butoxy)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.053 g, 0.098 mmol), (1-benzyl-1H-pyrazol-4-yl)boronic acid (0.039 g, 0.195 mmol) and 2.0 M aq. $Na_2CO_3$ (0.147 ml, 0.293 mmol) in DMF (1.5 ml) was sparged with nitrogen for 5 min, then treated with $Pd(Ph_3P)_4$ (7.90 mg, 6.84 μmol), and sparged for an additional 2 minutes. The flask was sealed and heated (85° C. oil bath) for 2 hrs, then cooled, diluted with water (3 mL), treated with 1.0N HCl (1 mL), and extracted with $Et_2O$ (2×10 mL). The combined organic extracts were concentrated and the residue was purified by biotage (12 g $SiO_2$, 0% (3 CV), 0-60% (15 CV), 60% (2 CV), EtOAc in hexanes). Product fractions were pooled and concentrated under reduced pressure, affording the product (0.011 g, 0.018 mmol, 18.17% yield) as a clear yellow oil. LCMS (M+H)=620.4.

Example 8

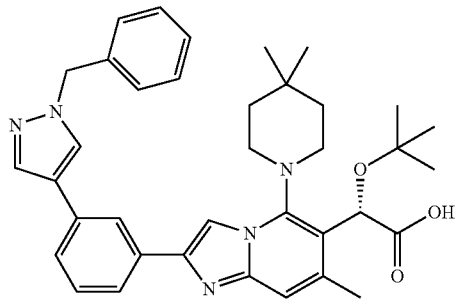 [SMILES: Cc1cc2nc(-c3cccc(-c4cnn(Cc5ccccc5)c4)c3)cn2c(N2CCC(C)(C)CC2)c1[C@H](OC(C)(C)C)C(=O)O]

(S)-2-(2-(3-(1-Benzyl-1H-pyrazol-4-yl)phenyl)-5-(4,4-dimethylpiperidin-1-yl)-7-methylimidazo[1,2-a]pyridin-6-yl)-2-(tert-butoxy)acetic Acid A solution of (S)-methyl 2-(2-(3-(1-benzyl-1H-pyrazol-4-yl)phenyl)-5-(4,4-dimethylpiperidin-1-yl)-7-methylimidazo[1,2-a]pyridin-6-yl)-2-(tert-butoxy)acetate (0.011 g, 0.018 mmol) in MeOH (1.5 mL) was treated with lithium hydroxide monohydrate (7.5 mg, 0.177 mmol) and stirred with heating (85° C. heating block) for 2.5 hrs. The reaction was cooled, filtered (0.45 syringe-tip filter) and the filtrate was purified by preparative LCMS. Product fractions were combined and dried via centrifugal evaporation, to afford (S)-2-(2-(3-(1-benzyl-1H-pyrazol-4-yl)phenyl)-5-(4,4-dimethylpiperidin-1-yl)-7-methylimidazo[1,2-a]pyridin-6-yl)-2-(tert-butoxy)acetic acid (0.008 g, 0.013 mmol, 74.4% yield) as a light gray solid. $^1$H NMR (400 MHz, CD$_3$OD) δ 8.21-8.13 (m, 3H), 7.99 (s, 1H), 7.78 (d, J=8.0 Hz, 1H), 7.60 (d, J=8.0 Hz, 1H), 7.52-7.44 (m, 1H), 7.41-7.25 (m, 6H), 6.01 (s, 1H), 5.41 (s, 2H), 3.84-3.71 (m, 1H), 3.67-3.55 (m, 1H), 3.38 (br. s., 1H), 3.04 (d, J=11.5 Hz, 1H), 2.54 (s, 3H), 1.84-1.69 (m, 2H), 1.59 (d, J=12.5 Hz, 1H), 1.52 (d, J=12.8 Hz, 1H), 1.27 (s, 9H), 1.22 (s, 3H), 1.10 (s, 3H). LCMS (M+H)=606.4.

Intermediate 21

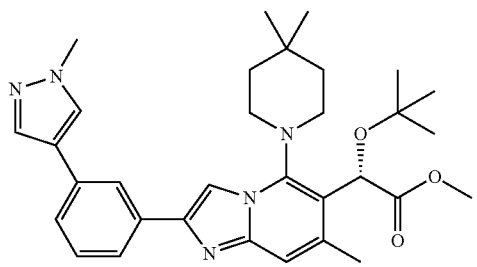

(S)-Methyl 2-(tert-butoxy)-2-(5-(4,4-dimethylpiperidin-1-yl)-7-methyl-2-(3-(1-methyl-1H-pyrazol-4-yl)phenyl)imidazo[1,2-a]pyridin-6-yl)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.050 g, 0.092 mmol), 1-methyl-4-(4,4,5,5-tetramethyl-1,3,2-dioxaborolan-2-yl)-1H-pyrazole (0.080 g, 0.384 mmol) and 2.0 M aq. Na$_2$CO$_3$ (0.230 ml, 0.461 mmol) in DMF (1.5 ml) was sparged with nitrogen for 5 min, then treated with Pd(Ph$_3$P)$_4$ (7.46 mg, 6.45 μmol), and sparged for an additional 2 minutes. The flask was sealed and heated (85° C. oil bath) for 2 hrs. LCMS (088-01): trace SM remains, large product peak. The reaction was cooled, diluted with water (3 mL), treated with 1.0N HCl (1 mL), and extracted with Et$_2$O (2×10 mL). The combined organic extracts were concentrated and the residue was purified by biotage (12 g SiO$_2$, 0% (3 CV), 0-60% (15 CV), 60% (2 CV), EtOAc in hexanes). Product fractions were pooled and concentrated under reduced pressure, affording the product (0.048 g), contaminated with residual triphenylphosphine oxide, as a clear film. LCMS (M+H)= 544.4.

Example 9

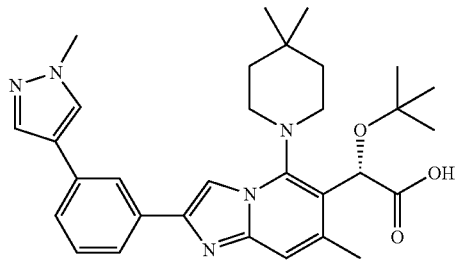 [SMILES: Cc1cc2nc(-c3cccc(-c4cnn(C)c4)c3)cn2c(N2CCC(C)(C)CC2)c1[C@H](OC(C)(C)C)C(=O)O]

(S)-2-(tert-Butoxy)-2-(5-(4,4-dimethylpiperidin-1-yl)-7-methyl-2-(3-(1-methyl-1H-pyrazol-4-yl)phenyl)imidazo[1,2-a]pyridin-6-yl)acetic Acid A solution of (S)-methyl 2-(tert-butoxy)-2-(5-(4,4-dimethylpiperidin-1-yl)-7-methyl-2-(3-(1-methyl-1H-pyrazol-4-yl)phenyl)imidazo[1,2-a]pyridin-6-yl)acetate (0.048 g, 0.088 mmol) in MeOH (1.5 mL) was treated with lithium hydroxide monohydrate (0.027 g, 0.643 mmol) and stirred for 2.5 hrs, then cooled, and filtered (0.45 μm syringe tip filter). The crude mixture was purified by preparative LCMS, and product fractions were combined and dried via centrifugal evaporation, to afford the desired product (0.0375 g, 0.071 mmol, 80% yield) as an off-white solid. 1H NMR (500 MHz, CD$_3$OD) δ 8.15 (t, J=1.6 Hz, 1H), 8.13 (s, 1H), 8.04 (s, 1H), 7.92 (d, J=0.6 Hz, 1H), 7.77 (dt, J=7.8, 1.3 Hz, 1H), 7.56 (dt, J=7.7, 1.3 Hz, 1H), 7.48-7.41 (m, 1H), 7.26 (s, 1H), 5.99 (s, 1H), 3.96 (s, 3H), 3.84-3.73 (m, 1H), 3.62 (td, J=11.5, 2.5 Hz, 1H), 3.43-3.36 (m, 1H), 3.07-3.00 (m, 1H), 2.53 (d, J=0.8 Hz, 3H), 1.82-1.71 (m, 2H), 1.59 (d, J=13.2 Hz, 1H), 1.52 (d, J=13.1 Hz, 1H), 1.26 (s, 9H), 1.22 (s, 3H), 1.10 (s, 3H). $^{13}$C NMR (101 MHz, CD$_3$OD) δ 177.3, 147.2, 147.1, 144.1, 144.0, 142.8, 142.5, 137.7, 134.7, 134.3, 130.6, 129.5, 126.5, 126.2, 125.4, 124.4, 124.2, 114.3, 108.6, 77.0, 71.1, 46.9, 45.4, 45.3, 40.6, 40.2, 39.2, 32.4, 29.7, 28.7, 25.4, 21.3. LCMS (M+H)=530.3.

Intermediate 22

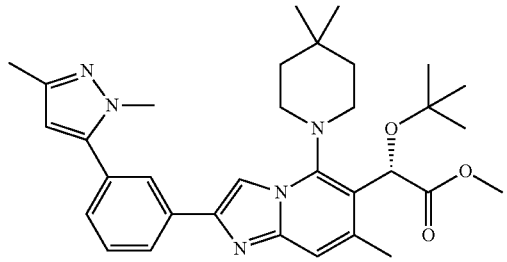

(S)-Methyl 2-(tert-butoxy)-2-(2-(3-(1,3-dimethyl-1H-pyrazol-5-yl)phenyl)-5-(4,4-dimethylpiperidin-1-yl)-7-methylimidazo[1,2-a]pyridin-6-yl)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.067 g, 0.124 mmol), (1,3-dimethyl-1H-pyrazol-5-yl)boronic acid (0.070 g, 0.500 mmol) and 2.0 M aq. Na$_2$CO$_3$ (0.247 ml, 0.494 mmol) in DMF (1.5 ml) was sparged with nitrogen for 5 min, then treated with Pd(Ph₃P)₄ (9.99 mg, 8.65 μmol), and sparged for an additional 2 minutes. The flask was sealed and heated (85° C. oil bath) for 2 hrs, then cooled, diluted with water (3 mL), treated with 1.0N HCl (1 mL), and extracted with Et₂O (2×10 mL). The combined organic extracts were concentrated and the residue was purified by biotage (12 g SiO₂, 0% (3 CV), 0-100% (15 CV), 1000% (2 CV), EtOAc in hexanes). Product fractions were pooled and concentrated under reduced pressure, affording the product as a clear film. LCMS (M+H)=558.3.

Example 10

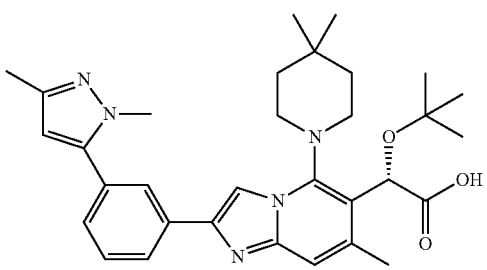 [SMILES: Cc1cc(-c2cccc(-c3cn4c(N5CCC(C)(C)CC5)c([C@H](OC(C)(C)C)C(=O)O)c(C)cc4n3)c2)n(C)n1]

(S)-2-(tert-Butoxy)-2-(2-(3-(1,3-dimethyl-1H-pyrazol-5-yl)phenyl)-5-(4,4-dimethylpiperidin-1-yl)-7-methylimidazo[1,2-a]pyridin-6-yl)acetic Acid A solution of (S)-methyl 2-(tert-butoxy)-2-(2-(3-(1,3-dimethyl-1H-pyrazol-5-yl)phenyl)-5-(4,4-dimethylpiperidin-1-yl)-7-methylimidazo[1,2-a]pyridin-6-yl)acetate (0.069 g, 0.124 mmol) in MeOH (1.5 mL) was treated with lithium hydroxide monohydrate (0.026 g, 0.620 mmol) and stirred with heating (85° C. heating block) for 2 hrs. The reaction was cooled, filtered (0.45 μm syringe tip filter) and purified by preparative LCMS. Product fractions were combined and dried via centrifugal evaporation, to afford the desired product (0.0598 g, 0.110 mmol, 89% yield) as an off-white solid. ¹H NMR (500 MHz, CD₃OD) δ 8.08 (s, 1H), 8.05 (t, J=1.6 Hz, 1H), 7.99 (dt, J=8.0, 1.2 Hz, 1H), 7.55 (t, J=7.7 Hz, 1H), 7.43-7.40 (m, 1H), 7.16 (s, 1H), 6.24 (s, 1H), 5.80 (br. s., 1H), 3.86 (s, 3H), 3.81-3.69 (m, 2H), 3.67-3.48 (m, 2H), 3.16-2.98 (m, 1H), 2.53 (d, J=0.9 Hz, 3H), 2.28 (s, 3H), 1.58 (d, J=12.9 Hz, 1H), 1.49 (d, J=13.1 Hz, 1H), 1.24 (s, 9H), 1.19 (s, 3H), 1.09 (s, 3H). ¹³C NMR (101 MHz, CD₃OD) δ 178.6, 177.8, 147.1, 146.4, 144.4, 142.6, 140.2, 140.0, 134.0, 130.5, 128.5, 127.3, 125.5, 125.4, 125.3, 112.8, 106.6, 104.9, 74.4, 70.7, 45.0, 43.5, 43.4, 38.8, 38.5, 35.5, 27.8, 27.0, 22.5, 19.7, 11.5. LCMS (M+H)=544.4.

Intermediate 23

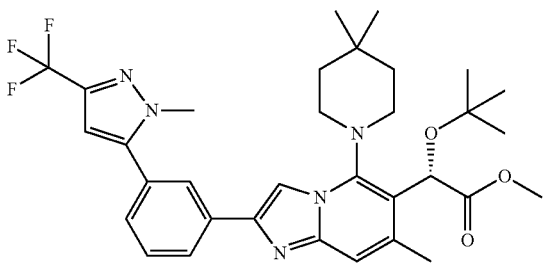

(S)-Methyl 2-(tert-butoxy)-2-(5-(4,4-dimethylpiperidin-1-yl)-7-methyl-2-(3-(1-methyl-3-(trifluoromethyl)-1H-pyrazol-5-yl)phenyl) imidazo[1,2-a]pyridin-6-yl)acetate A solution of (S)-methyl 2-(2-(3-bromophenyl)-5-(4,4-dimethylpiperidin-1-yl)-7-methylimidazo[1,2-a]pyridin-6-yl)-2-(tert-butoxy)acetate (0.051 g, 0.094 mmol), (1-methyl-3-(trifluoromethyl)-1H-pyrazol-5-yl)boronic acid (0.036 g, 0.188 mmol) and 2.0 M aq. Na₂CO₃ (0.141 ml, 0.282 mmol) in DMF (1.5 ml) was sparged with nitrogen for 5 min, then treated with Pd(Ph₃P)₄ (7.60 mg, 6.58 μmol), and sparged for an additional 2 minutes. The flask was sealed and heated (85° C. oil bath) for 2 hrs, then cooled. The reaction was purified by biotage (12 g SiO₂, 0% (3 CV), 0-100% (15 CV), 100% (2 CV), EtOAc in hexanes). Product fractions were pooled and concentrated under reduced pressure, affording the product and residual DMF. LCMS (M+H)=612.3.

Example 11

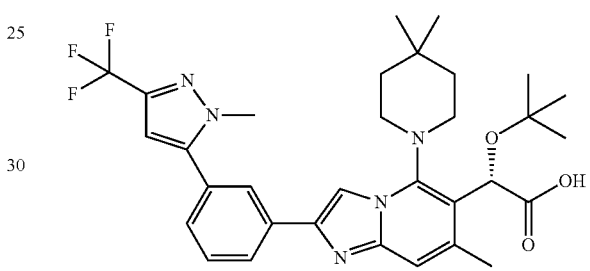

(S)-2-(tert-Butoxy)-2-(5-(4,4-dimethylpiperidin-1-yl)-7-methyl-2-(3-(1-methyl-3-(trifluoromethyl)-1H-pyrazol-5-yl)phenyl)imidazo[1,2-a]pyridin-6-yl) acetic Acid A solution of (S)-methyl 2-(tert-butoxy)-2-(5-(4,4-dimethylpiperidin-1-yl)-7-methyl-2-(3-(1-methyl-3-(trifluoromethyl)-1H-pyrazol-5-yl)phenyl)imidazo[1,2-a]pyridin-6-yl)acetate (0.057 g, 0.094 mmol) in MeOH (2 mL) was treated with lithium hydroxide monohydrate (0.024 g, 0.572 mmol) and the mixture was heated (85° C. heating block) for 16 hrs. The reaction was treated with additional lithium hydroxide monohydrate (0.104 g, 2.48 mmol), stirred for 3.5 hrs, then cooled, and filtered (0.45 m syringe tip filter). The filtrate was purified by preparative LCMS, and product fractions were combined and dried via centrifugal evaporation, to afford the desired product (0.0476 g, 0.076 mmol, 80% yield) as a light gray solid. ¹H NMR (500 MHz, CD₃OD) δ 8.19 (s, 1H), 8.14 (t, J=1.6 Hz, 1H), 8.08 (dt, J=8.0, 1.3 Hz, 1H), 7.62 (t, J=7.7 Hz, 1H), 7.52 (dt, J=7.9, 1.2 Hz, 1H), 7.25 (s, 1H), 6.78 (s, 1H), 6.02 (s, 1H), 4.00 (s, 3H), 3.84-3.75 (m, 1H), 3.62 (td, J=11.5, 2.2 Hz, 1H), 3.39-3.32 (m, 1H), 3.04-2.97 (m, 1H), 2.52 (d, J=0.9 Hz, 3H), 1.83-1.70 (m, 2H), 1.58 (d, J=13.1 Hz, 1H), 1.51 (d, J=13.4 Hz, 1H), 1.27 (s, 9H), 1.21 (s, 3H), 1.09 (s, 3H). ¹³C NMR (101 MHz, CD₃OD) δ 147.9, 146.8, 144.1, 142.9, 142.7, 142.4, 141.7, 135.3, 131.3, 130.7, 129.8, 128.3, 127.8, 125.6, 124.3, 121.7, 115.0, 109.1, 105.6, 105.5, 77.1, 70.8, 46.9, 45.4, 45.3, 40.6, 40.2, 38.7, 32.6, 29.6, 28.7, 25.2, 21.2. LCMS (M+H)=598.3.

Intermediate 24

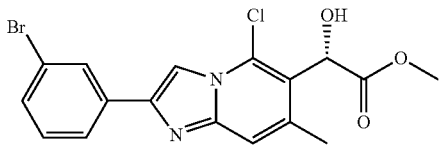

(S)-Methyl 2-(2-(3-bromophenyl)-5-chloro-7-methylimidazo[1,2-a]pyridin-6-yl)-2-hydroxyacetate To a stirred brown solution of methyl 2-(2-(3-bromophenyl)-5-chloro-7-methylimidazo[1,2-a]pyridin-6-yl)-2-oxoacetate (1.67 g, 4.10 mmol) and (R)-1-methyl-3,3-diphenylhexahydropyrrolo[1,2-c][1,3,2]oxazaborole (0.227 g, 0.819 mmol) in anhydrous toluene (40 mL) was added dropwise 50% catecholborane (1.316 ml, 6.15 mmol) over 15 min at −45° C. The reaction mixture was stirred for 3 hrs while slowly warming to −10 C. Then, diluted with EtOAc (150 mL), washed with sat. Na$_2$CO$_3$ by vigorously stirring for 10 min each time (5×25 mL), dried (MgSO$_4$), filtered, concentrated and filtered through plug of silica gel (2'×5') using EtOAc and concentrated to give crude product (1.36 g, 3.32 mmol, 81% yield) as light purple solid which was used in the next step without further purification. 1H NMR (500 MHz, CDCl$_3$) δ 8.15 (t, J=1.7 Hz, 1H), 8.04 (d, J=0.5 Hz, 1H), 7.91 (qd, J=0.9, 7.7 Hz, 1H), 7.50 (ddd, J=1.1, 2.0, 8.0 Hz, 1H), 7.42 (s, 1H), 7.33 (t, J=7.9 Hz, 1H), 5.76 (s, 1H), 3.86 (s, 3H), 3.62 (br. s., 1H), 2.46 (d, J=1.0 Hz, 3H). LCMS (M+H)=411.0.

Intermediate 25

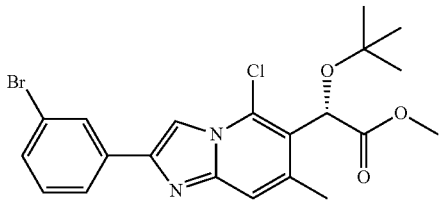

(S)-Methyl 2-(2-(3-bromophenyl)-5-chloro-7-methylimidazo[1,2-a]pyridin-6-yl)-2-(tert-butoxy)acetate A stirred solution of (S)-methyl 2-(2-(3-bromophenyl)-5-chloro-7-methylimidazo[1,2-a]pyridin-6-yl)-2-hydroxyacetate (1.35 g, 3.30 mmol) and 70% HClO$_4$ (0.312 ml, 3.62 mmol) in DCM (150 mL, HPLC grade) was cooled in an ice-water bath and saturated with isobutylene by bubbling through the reaction mixture for 10 min. After 1 hr, the cold bath was removed and the resulting tan slurry/turbid reaction mixture was stirred at rt for 15 hrs. The homogeneous brown solution was washed with sat Na$_2$CO$_3$ (10 mL), dried (MgSO$_4$), filtered, concentrated and purified by flash chromatography using 10, 20 and 30% EtOAc/Hex followed by 10% MeOH/EtOAc to afford the product (1.1163 g, 2.397 mmol, 72.7% yield) as a white solid. $^1$H NMR (500 MHz, CDCl$_3$) δ 8.15 (t, J=1.7 Hz, 1H), 8.03 (s, 1H), 7.90 (qd, J=0.9, 7.7 Hz, 1H), 7.46-7.50 (m, 1H), 7.39 (s, 1H), 7.33 (t, J=7.9 Hz, 1H), 5.67 (s, 1H), 3.75 (s, 3H), 2.50 (d, J=0.9 Hz, 3H), 1.28 (s, 9H). LCMS (M+H)=467.1.

Intermediate 26

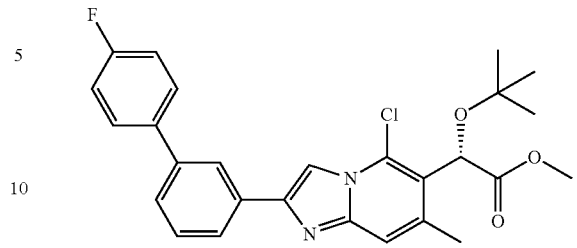

(S)-Methyl 2-(tert-butoxy)-2-(5-chloro-2-(4'-fluoro-[1,1'-biphenyl]-3-yl)-7-methylimidazo[1,2-a]pyridin-6-yl)acetate A solution of (S)-methyl 2-(2-(3-bromophenyl)-5-chloro-7-methylimidazo[1,2-a]pyridin-6-yl)-2-(tert-butoxy)acetate (0.066 g, 0.142 mmol), (4-fluorophenyl)boronic acid (0.024 g, 0.172 mmol) and 2.0 M aq. Na$_2$CO$_3$ (0.213 ml, 0.425 mmol) in DMF (1.0 ml) was sparged with nitrogen for 5 min, then treated with Pd(Ph$_3$P)$_4$ (0.011 g, 9.92 μmol), and sparged for an additional 2 minutes. The flask was sealed and heated (85° C. heating block) for 2 hrs, then cooled and the reaction was diluted with water (3 mL), treated with 1.0N HCl (1 mL), and extracted with Et$_2$O (2×10 mL). The combined organic extracts were dried (MgSO$_4$), concentrated and the residue was purified by biotage (12 g SiO$_2$, 0% (3 CV), 0-60% (15 CV), 60% (2 CV), EtOAc in hexanes). Product fractions were pooled and concentrated under reduced pressure, affording a clear film. The residue was further purified by preparative HPLC, and product fractions were pooled and concentrated under reduced pressure, affording the product (0.035 g, 0.073 mmol, 51.4% yield) as a clear film. $^1$H NMR (500 MHz, CDCl$_3$) δ 8.19-8.14 (m, 1H), 8.06 (s, 1H), 7.92 (dt, J=6.8, 1.8 Hz, 1H), 7.71-7.61 (m, 2H), 7.58-7.48 (m, 2H), 7.44 (s, 1H), 7.21-7.10 (m, 2H), 5.66 (s, 1H), 3.73 (s, 3H), 2.50 (d, J=0.8 Hz, 3H), 1.27 (s, 9H). LCMS (M+H)=481.2.

Intermediate 27

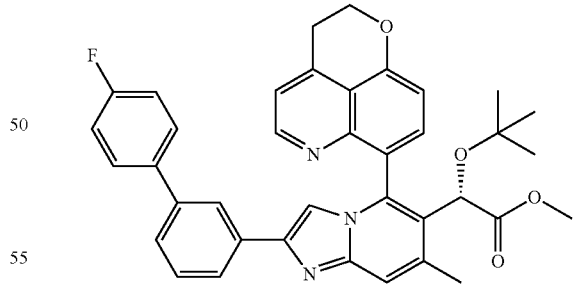

(2S)-Methyl 2-(tert-butoxy)-2-(5-(2,3-dihydropyrano[4,3,2-de]quinolin-7-yl)-2-(4'-fluoro-[1,1'-biphenyl]-3-yl)-7-methylimidazo[1,2-a]pyridin-6-yl)acetate A mixture of (S)-methyl 2-(tert-butoxy)-2-(5-chloro-2-(4'-fluoro-[1,1'-biphenyl]-3-yl)-7-methylimidazo[1,2-a]pyridin-6-yl)acetate (0.067 g, 0.139 mmol), (2,3-dihydropyrano[4,3,2-de]quinolin-7-yl)boronic acid (0.060 g, 0.279 mmol;

ref: WO2009062285) and 2M Na₂CO₃ (0.209 ml, 0.418 mmol) in DMF (2 mL) was degassed for 10 min. Then, Pd(Ph₃P)₄ (0.016 g, 0.014 mmol) was added, degassed for 5 min and heated at 120° C. for 3 hrs using Biotage microwave. The mixture was cooled and purified by prep-HPLC to afford the product (0.04675 g, 0.076 mmol, 54.5% yield) as a light brown solid. LCMS (M+H)=616.2.

Example 12 and 13

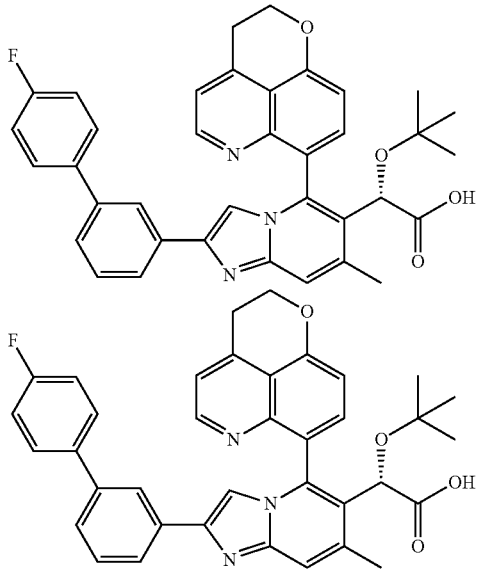

(2S)-2-(tert-Butoxy)-2-(5-(2,3-dihydropyrano[4,3,2-de]quinolin-7-yl)-2-(4'-fluoro-[1,1'-biphenyl]-3-yl)-7-methylimidazo[1,2-a]pyridin-6-yl)acetic Acid.TFA A mixture of (2S)-methyl 2-(tert-butoxy)-2-(5-(2,3-dihydropyrano[4,3,2-de]quinolin-7-yl)-2-(4'-fluoro-[1,1'-biphenyl]-3-yl)-7-methylimidazo[1,2-a]pyridin-6-yl)acetate (0.037 g, 0.060 mmol) and LiOH (0.014 g, 0.601 mmol) in 9:1 MeOH/H₂O (2 mL) was refluxed for 3 hrs, then cooled and purified by prep-HPLC, affording two atropisomeric compounds.

Example 12

First eluting atropisomer (0.0303 g, 0.042 mmol, 70.4% yield), brown solid. ¹H NMR (500 MHz, CDCl₃) δ 8.77 (d, J=4.6 Hz, 1H), 8.24 (s, 1H), 8.09 (t, J=1.6 Hz, 1H), 7.81 (d, J=6.6 Hz, 1H), 7.65-7.70 (m, 2H), 7.58 (td, J=1.3, 7.7 Hz, 1H), 7.52-7.55 (m, 1H), 7.43 (t, J=7.7 Hz, 2H), 7.31-7.35 (m, 1H), 7.12-7.19 (m, 2H), 6.92 (s, 1H), 5.01 (br. s., 1H), 4.64-4.77 (m, 2H), 3.43-3.54 (m, 2H), 2.77 (s, 3H), 0.93 (br. s., 9H). LCMS (M+H)=602.2.

Example 13

Second eluting atropisomer (0.0045 g, 6.29 μmol, 10.46% yield), white solid. 1H NMR (500 MHz, CDCl₃) δ 8.65 (d, J=4.3 Hz, 1H), 8.22 (s, 1H), 8.19 (d, J=8.0 Hz, 1H), 7.65-7.70 (m, 2H), 7.57 (d, J=7.7 Hz, 1H), 7.50 (d, J=7.7 Hz, 1H), 7.38-7.44 (m, 1H), 7.22-7.27 (m, 2H), 7.14 (t, J=8.7 Hz, 2H), 6.85 (s, 1H), 5.15 (s, 1H), 4.65 (t, J=5.9 Hz, 2H), 3.35-3.45 (m, 2H), 2.63 (s, 3H), 0.83 (s, 9H). LCMS (M+H)=602.3.

Intermediate 28

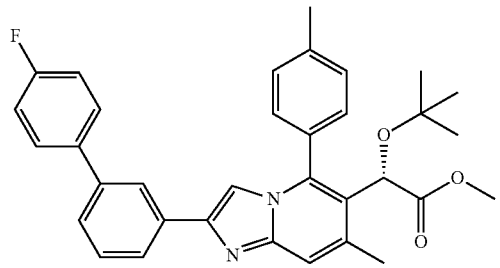

(S)-Methyl 2-(tert-butoxy)-2-(2-(4'-fluoro-[1,1'-biphenyl]-3-yl)-7-methyl-5-(p-tolyl)imidazo[1,2-a]pyridin-6-yl)acetate A solution of (S)-methyl 2-(tert-butoxy)-2-(5-chloro-2-(4'-fluoro-[1,1'-biphenyl]-3-yl)-7-methylimidazo[1,2-a]pyridin-6-yl)acetate (0.035 g, 0.073 mmol) and p-tolylboronic acid (0.020 g, 0.146 mmol) in DMF (1.5 mL) was treated with 2.0 M aq. Na₂CO₃ (0.109 mL, 0.218 mmol). The mixture was sparged for 5 min with N2 stream, then treated with Pd(Ph₃P)₄ (5.89 mg, 5.09 μmol), sparged for 2 min, and sealed and heated (85° C. heating block) for 1 hr. The reaction was treated with additional Pd(Ph₃P)₄ (5.89 mg, 5.09 μmol), sparged for 3 min, and then heated (120° C. microwave) for 1 hr. The reaction was diluted with water (2 mL) and extracted with Et₂O (2×5 mL). The combined extracts were dried (MgSO₄), filtered, and concentrated under reduced pressure. The residue was purified by biotage (12 g SiO₂, 0% (3 CV), 0-80% (15 CV), 80% (2 CV), EtOAc in hexanes). Product fractions were pooled and concentrated under reduced pressure, affording the product (0.0103 g, 0.019 mmol, 26.4% yield). LCMS (M+H)=537.3.

Example 14

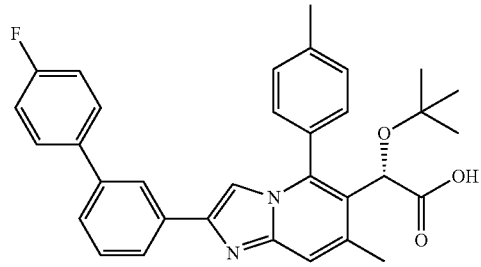 [SMILES: Cc1ccc(-c2c([C@H](OC(C)(C)C)C(=O)O)c(C)cc3nc(-c4cccc(-c5ccc(F)cc5)c4)cn23)cc1]

(S)-2-(tert-butoxy)-2-(2-(4'-fluoro-[1,1'-biphenyl]-3-yl)-7-methyl-5-(p-tolyl)imidazo[1,2-a]pyridin-6-yl) acetic Acid A solution of (S)-methyl 2-(tert-butoxy)-2-(2-(4'-fluoro-[1,1'-biphenyl]-3-yl)-7-methyl-5-(p-tolyl)imidazo[1,2-a]pyridin-6-yl)acetate (0.0103 g, 0.019 mmol) in MeOH (1.5 mL) was treated with lithium hydroxide monohydrate (4.03 mg, 0.096 mmol) and stirred with heating (85° C. heating block) for 2 hrs. The crude reaction was purified by preparative LCMS, and product fractions were combined and dried via centrifugal evaporation, to afford the desired product (0.0068 g, 0.013 mmol, 67.8% yield) as an off-white solid. LCMS (M+H)=523.2.

Intermediate 29

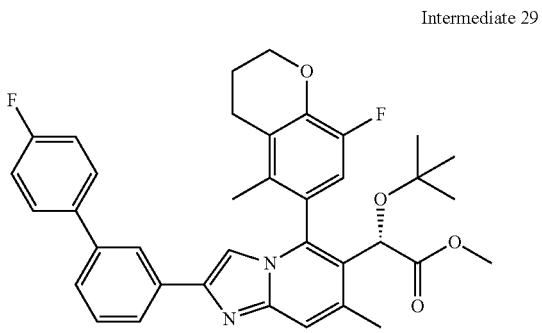 [SMILES: COC(=O)[C@@H](OC(C)(C)C)c1c(C)cc2nc(-c3cccc(-c4ccc(F)cc4)c3)cn2c1-c1cc(F)c2c(c1C)CCCO2]

(2S)-Methyl 2-(tert-butoxy)-2-(5-(8-fluoro-5-methylchroman-6-yl)-2-(4'-fluoro-[1,1'-biphenyl]-3-yl)-7-methylimidazo[,2-a]pyridin-6-yl)acetate A solution of (S)-methyl 2-(tert-butoxy)-2-(5-chloro-2-(4'-fluoro-[1,1'-biphenyl]-3-yl)-7-methylimidazo[1,2-a]pyridin-6-yl)acetate (0.042 g, 0.087 mmol), (8-fluoro-5-methylchroman-6-yl)boronic acid (0.028 g, 0.131 mmol; ref: WO2009062285), palladium(II) acetate (1.961 mg, 8.73 µmol), 2-dicyclohexylphosphino-2',6'-dimethoxy-1,1'-biphenyl (S-phos, 6.1 mg, 0.015 mmol) and potassium phosphate, tri-basic (0.056 g, 0.262 mmol) in dioxane (0.8 ml) and water (0.200 ml) was nitrogen gas sparged for 5 min, then sealed and heated (65° C. heating block) for 5 hrs, then cooled. The mixture was diluted with water (5 mL) and extracted with Et$_2$O (2×5 mL), and the combined extracts were dried (MgSO$_4$), filtered, and concentrated under reduced pressure. The residue was purified by biotage (12 g SiO$_2$, 20% (3 CV), 20-100% (15 CV), 100% (2 CV), EtOAc in hexanes). Product fractions were pooled and concentrated under reduced pressure, affording the desired product (0.023 g, 0.038 mmol, 43.1% yield), as a yellow film. LCMS (M+H)=611.3.

Example 15 and 16

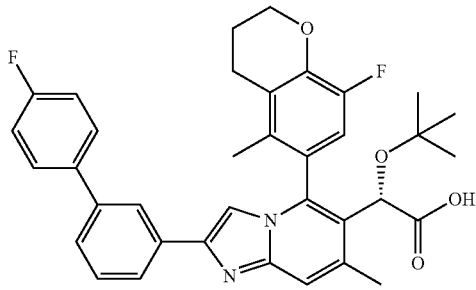

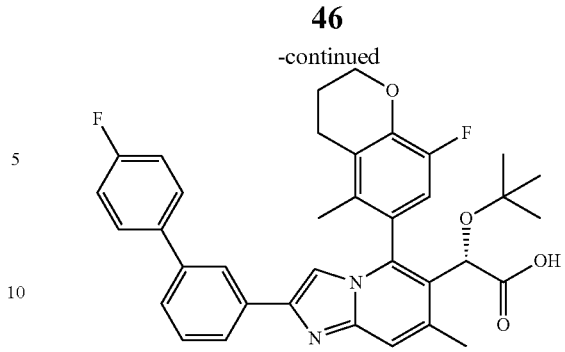

(2S)-2-(tert-Butoxy)-2-(5-(8-fluoro-5-methylchroman-6-yl)-2-(4'-fluoro-[1,1'-biphenyl]-3-yl)-7-methylimidazo[1,2-a]pyridin-6-yl)acetic Acid A solution of (2S)-methyl 2-(tert-butoxy)-2-(5-(8-fluoro-5-methylchroman-6-yl)-2-(4'-fluoro-[1,1'-biphenyl]-3-yl)-7-methylimidazo[1,2-a]pyridin-6-yl)acetate (0.023 g, 0.038 mmol) in methanol (1.5 mL) was treated with lithium hydroxide monohydrate (0.016 g, 0.377 mmol), and the reaction was stirred with heating (85° C. heating block) for 3 hrs. The reaction mixture was purified by prep-LCMS, affording two atropisomeric compounds.

Example 15

First eluting atopisomer (0.0036 g, 6.03 µmol, 16.02% yield), brown solid. LCMS (M+H)=597.3.

Example 16

Second eluting atopisomer (0.0082 g, 0.014 mmol, 36.5% yield), brown solid. $^1$H NMR (400 MHz, CD$_3$OD) δ: 8.08 (s, 1H), 7.76 (d, J=8.0 Hz, 1H), 7.70 (dd, J=8.8, 5.3 Hz, 2H), 7.55 (d, J=7.8 Hz, 1H), 7.47 (d, J=7.8 Hz, 1H), 7.44 (s, 1H), 7.29 (s, 1H), 7.18 (t, J=8.8 Hz, 2H), 6.98 (d, J=10.8 Hz, 1H), 5.00 (s, 1H), 4.36-4.28 (m, 2H), 2.86-2.77 (m, 2H), 2.64 (s, 3H), 2.22-2.12 (m, 2H), 1.91 (s, 3H), 1.16 (s, 9H). LCMS (M+H)=597.3.

Example 17

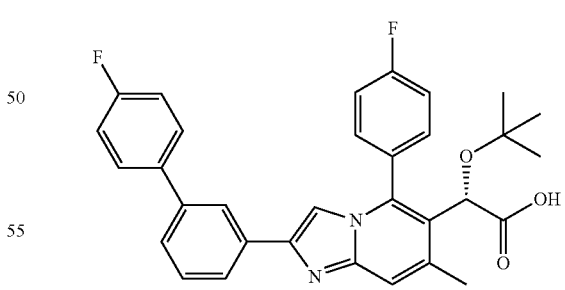

(S)-2-(tert-Butoxy)-2-(2-(4'-fluoro-[1,1'-biphenyl]-3-yl)-5-(4-fluorophenyl)-7-methylimidazo[1,2-a]pyridin-6-yl)acetic Acid This material was isolated as a by-product from the preparation of the preceeding example, affording the product (0.0044 g, 8.36 µmol, 22.19% yield) as a brown solid. LCMS (M+H)=527.2.

Example 18

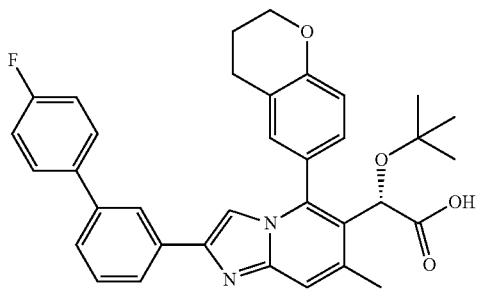 [SMILES: Cc1cc2nc(-c3cccc(-c4ccc(F)cc4)c3)cn2c(-c2ccc3c(c2)CCCO3)c1[C@H](OC(C)(C)C)C(=O)O]

(S)-2-(tert-Butoxy)-2-(5-(chroman-6-yl)-2-(4'-fluoro-[1,1'-biphenyl]-3-yl)-7-methylimidazo[1,2-a]pyridin-6-yl)acetic Acid (S)-methyl 2-(2-(3-bromophenyl)-5-chloro-7-methylimidazo[1,2-a]pyridin-6-yl)-2-(tert-butoxy)acetate (0.075 g, 0.16 mmol), chroman-6-ylboronic acid (0.056 g, 0.31 mmol), Cs2CO3 (0.102 g, 0.312 mmol), PdOAc2 (3.5 mg, 0.016 mmol), and 2-dicyclohexylphosphino-2',6'-dimethoxybiphenyl (SPhos) (0.013 g, 0.031 mmol) were combined in a sealed reaction vessel. The dry mixture was evacuated and charged with N2 (3×). The solids were then taken up in a mixture of DMF (2 mL)/Water (0.2 mL) and heated to 80° C. The mixture was stirred at this temp for two hours. The mixture was diluted with EtOAc and washed with sat aq NH4Cl. The layers were separated and the aq layer was extracted with EtOAc (2×10 mL). The combined organic extracts were washed with brine, dried over Na2SO4, filtered and concentrated to give a yellow oil. This oil was adsorbed onto Celite, and then purified on silica gel eluting with a 0-75% EtOAc in hexanes gradient over 12 CV to give (S)-methyl 2-(tert-butoxy)-2-(5-(chroman-6-yl)-2-(4'-fluoro-[1,1'-biphenyl]-3-yl)-7-methylimidazo[1,2-a]pyridin-6-yl)acetate (22 mg, 0.038 mmol, 24% yield) as a semi-pure yellow oil. LCMS (M+H): 579.

LiOH (0.95 mg, 0.040 mmol) was added to a stirring solution of (S)-methyl 2-(tert-butoxy)-2-(5-(chroman-6-yl)-2-(4'-fluoro-[1,1'-biphenyl]-3-yl)-7-methylimidazo[1,2-a]pyridin-6-yl)acetate (23 mg, 0.040 mmol) in a 10:1 mixture of MeOH (2 mL) and water (0.2 mL). The mixture was heated to 75° C. The clear colorless solution was stirred at this temp for 3 h. The solution was concentrated to an aq mixture. The solids were neutralized with the addition of sat aq NH4Cl. The mixture was diluted with EtOAc. The layers were separated and the aq layer was extracted with EtOAc (2×10 mL). The combined organic extracts were washed with water, dried over Na2SO4, filtered and conc. to give a white solid. This solid was purified via preparative HPLC with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 70 minutes, then a 5-minute hold at 100% B; Flow: 20 mL/min. Fractions containing the desired product were combined and dried via centrifugal evaporation to give (S)-2-(tert-butoxy)-2-(5-(chroman-6-yl)-2-(4'-fluoro-[1,1'-biphenyl]-3-yl)-7-methylimidazo[1,2-a]pyridin-6-yl)acetic acid (6.7 mg, 0.011 mmol, 30%) as a white solid. ¹H NMR (500 MHz, DMSO-d6) δ 8.15 (d, J=7.0 Hz, 1H), 7.91 (t, J=6.8 Hz, 1H), 7.75 (d, J=7.3 Hz, 2H), 7.72 (d, J=8.8 Hz, 1H), 7.53 (d, J=7.3 Hz, 1H), 7.48-7.24 (m, 6H), 7.00 (t, J=6.6 Hz, 1H), 4.88 (d, J=11.0 Hz, 1H), 3.50 (br. m., J=7.0 Hz, 2H), 2.92-2.68 (m, 2H), 2.43 (br. s., 3H), 1.99 (br. m., 2H), 0.90 (s, 9H). LCMS (M+H): 467.

Intermediate 30

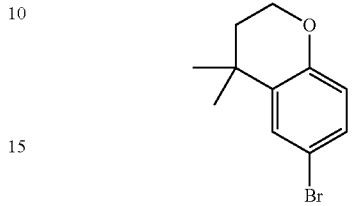

6-Bromo-4,4-dimethylchroman

Dimethylzinc (9.69 ml, 9.69 mmol) was added to a stirring solution of TiCl4 (9.69 ml, 9.69 mmol) in DCM (8.81 ml) at −30° C. The reaction mixture was stirred for 20 min. 6-Bromochroman-4-one (1 g, 4.40 mmol) in DCM (3 mL) was added drop wise to the reaction mixture. The mixture was then stirred at rt 16 h. The mixture was poured onto ice and extract with Et2O and wash with sat aq sodium bicarbonate. The organic phase was concentrated, adsorbed onto Celite and was purified on silica gel (Biotage, EtOAc/hexanes gradient) to give 6-bromo-4,4-dimethylchroman (883 mg, 3.66 mmol, 83% yield) as a white solid. ¹H NMR (500 MHz, CDCl3) δ 7.35 (d, J=2.5 Hz, 1H), 7.15 (dd, J=8.7, 2.5 Hz, 1H), 6.67 (d, J=8.7 Hz, 1H), 4.21-4.15 (m, 2H), 1.86-1.78 (m, 2H), 1.54 (s, 2H), 1.33 (s, 6H).

Intermediate 31

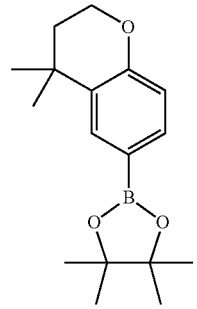

2-(4,4-Dimethylchroman-6-yl)-4,4,5,5-tetramethyl-1,3,2-dioxaborolane

6-Bromo-4,4-dimethylchroman (883 mg, 3.66 mmol)), B2Pin2 (1.02 g, 4.03 mmol)), PdCl2(dppf) (134 mg, 0.183 mmol), potassium acetate (7.08 g, 11.0 mmol) were combined in 1,4-dioxane (1.83E+04 μl)) at rt, degassed, back filled with N2, and warmed to 95° C. The reaction was allowed to stir at this temp for 3 h. The reaction was concentrated, adsorbed onto Celite and was purified on silica gel (Biotage, EtOAc/hexanes gradient) to give to give the expected product 2-(4,4-dimethylchroman-6-yl)-4,4,5,5-tetramethyl-1,3,2-dioxaborolane (1.16 g, 4.03 mmol, 110% yield) as a white solid. 1H NMR (500 MHz, CDCl3) δ 7.73 (d, J=1.4 Hz, 1H), 7.54 (dd, J=8.1, 1.5 Hz, 1H), 6.78 (d, J=8.0 Hz, 1H), 4.26-4.19 (m, 2H), 1.87-1.82 (m, 2H), 1.37 (s, 6H), 1.34 (s, 12H). LCMS (M+H): 289.

Example 19

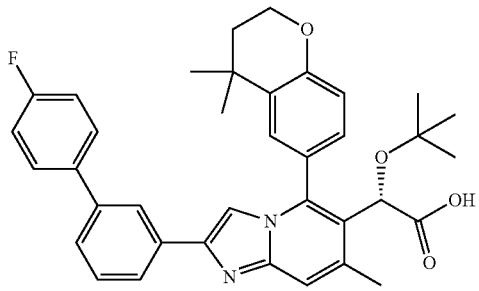 [SMILES: Cc1cc2nc(-c3cccc(-c4ccc(F)cc4)c3)cn2c(-c2ccc3c(c2)C(C)(C)CCO3)c1[C@H](OC(C)(C)C)C(=O)O]

(S)-2-(tert-Butoxy)-2-(5-(4,4-dimethylchroman-6-yl)-2-(4'-fluoro-[1,1'-biphenyl]-3-yl)-7-methylimidazo[1,2-a]pyridin-6-yl)acetic Acid (S)-Methyl 2-(2-(3-bromophenyl)-5-chloro-7-methylimidazo[1,2-a]pyridin-6-yl)-2-(tert-butoxy)acetate (0.075 g, 0.160 mmol), 2-(4,4-dimethylchroman-6-yl)-4,4,5,5-tetramethyl-1,3,2-dioxaborolane (0.090 g, 0.31 mmol), Cs2CO3 (0.102 g, 0.312 mmol), PdOAc2 (3.5 mg, 0.016 mmol), and 2-dicyclohexylphosphino-2',6'-dimethoxybiphenyl (SPhos) (0.013 g, 0.031 mmol) were combined in a sealed reaction vessel. The dry mixture was evacuated and charged with N2 (3×). The solids were then taken up in a mixture of DMF (2 mL)/Water (0.2 mL) and heated to 80° C. The mixture was stirred at this temp for two h. The mixture was diluted with EtOAc and washed with sat aq NH4Cl. The layers were separated and the aq layer was extracted with EtOAc (2×10 mL). The combined organic extracts were washed with brine, dried over Na2SO4, filtered and concentrated to give a yellow oil. This oil was adsorbed onto Celite, and then passed over a silica gel column eluting with a 0-75% EtOAc in hexanes gradient over 12 CV to give (S)-methyl 2-(tert-butoxy)-2-(5-(4,4-dimethylchroman-6-yl)-2-(4'-fluoro-[1,1'-biphenyl]-3-yl)-7-methylimidazo[1,2-a]pyridin-6-yl)acetate (25 mg, 0.041 mmol, 26% yield) as a semi-pure yellow oil. LCMS (M+H): 607.

LiOH (0.99 mg, 0.041 mmol) was added to a stirring solution of (S)-methyl 2-(tert-butoxy)-2-(5-(4,4-dimethylchroman-6-yl)-2-(4'-fluoro-[1,1'-biphenyl]-3-yl)-7-methylimidazo[1,2-a]pyridin-6-yl)acetate (25 mg, 0.041 mmol) in a 10:1 mixture of MeOH (2 mL) and water (0.2 mL). The mixture was heated to 75° C. The clear colorless solution was stirred at this temp for 3 h. The solution was concentrated to an aq mixture. The solids were neutralized with the addition of sat aq NH4Cl. The mixture was diluted with EtOAc. The layers were separated and the aq layer was extracted with EtOAc (2×10 mL). The combined organic extracts were washed with water, dried over Na2SO4, filtered and conc. to give a white solid. This solid was purified via preparative HPLC with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 30 minutes, then a 5-minute hold at 100% B; Flow: 20 mL/min. Fractions containing the desired product were combined and dried via centrifugal evaporation to give (S)-2-(tert-butoxy)-2-(5-(4, 4-dimethylchroman-6-yl)-2-(4'-fluoro-[1,1'-biphenyl]-3-yl)-7-methylimidazo[1,2-a]pyridin-6-yl)acetic acid (9.6 mg, 0.016 mmol, 39%) as a white solid as a mixture of rotomers/atropisomers. 1H NMR (500 MHz, DMSO-d6) δ 8.17 (s, 1H), 7.95-7.87 (m, 1H), 7.80-7.67 (m, 3H), 7.67-7.61 (m, 1H), 7.53 (d, J=7.7 Hz, 1H), 7.49-7.34 (m, 3H), 7.28 (t, J=8.8 Hz, 2H), 7.04-6.96 (m, 1H), 4.95 (s, 1H), 3.44 (br. m., 2H), 2.43 (s, 3H), 1.91-1.81 (m, 2H), 1.38 (s, 1H), 1.30 (d, J=3.3 Hz, 4H), 1.21 (s, 1H), 0.90-0.77 (m, 9H). LCMS (M+H): 593.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

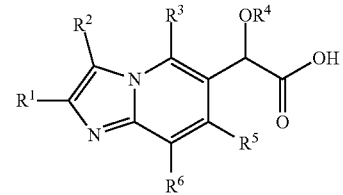

where:
$R^1$ is phenyl substituted with 1 $Ar^1$ substituent and also substituted with 0-3 substituents selected from halo, cyano, alkyl, haloalkyl, alkoxy, haloalkoxy, and alkenyloxy;
$R^2$ is hydrogen or alkyl;
$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or $R^3$ is cycloalkyl, cycloalkenyl, phenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
$R^4$ is alkyl or haloalkyl;
$R^5$ is hydrogen or alkyl;
$R^6$ is hydrogen or alkyl;
$Ar^1$ is phenyl, pyridinyl, pyridazinyl, pyrimidinyl, pyrazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, or tetrazolyl, and is substituted with 0-3 substituents selected from halo, cyano, alkyl, haloalkyl, benzyl, alkoxy, haloalkoxy, alkenyloxy, and benzyloxy;
or a pharmaceutically acceptable salt thereof.
2. A compound of claim 1 where:
$R^1$ is phenyl substituted with 1 $Ar^1$ substituent;
$R^2$ is hydrogen;

R³ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

or R³ is phenyl, chromanyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

R⁴ is alkyl;
R⁵ is alkyl;
R⁶ is hydrogen;

Ar¹ is phenyl or pyrazolyl, and is substituted with 0-3 substituents selected from halo, cyano, alkyl, haloalkyl, benzyl, alkoxy, haloalkoxy, alkenyloxy, and benzyloxy;

or a pharmaceutically acceptable salt thereof.

3. A compound of claim 1 where R¹ is phenyl substituted with 1 Ar¹ substituent.

4. A compound of claim 1 where R² is hydrogen, R⁴ is alkyl, R⁵ is alkyl, and R⁶ is hydrogen.

5. A compound of claim 1 where R³ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

6. A compound of claim 1 where R³ is phenyl, chromanyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

7. A compound of claim 1 where Ar¹ is phenyl, pyridinyl, pyridazinyl, pyrimidinyl, or pyrazinyl, and is substituted with 0-3 substituents selected from halo, cyano, alkyl, haloalkyl, benzyl, alkoxy, haloalkoxy, alkenyloxy, and benzyloxy.

8. A compound of claim 1 where Ar¹ is phenyl substituted with 0-3 substituents selected from halo, cyano, alkyl, haloalkyl, alkoxy, haloalkoxy, alkenyloxy, and benzyloxy.

9. A compound of claim 1 where Ar¹ is pyrrolyl, furanyl, thienyl, pyrazolyl, isoxazolyl, isothiazolyl, imidazolyl, oxazolyl, thiazolyl, triazolyl, oxadiazolyl, thiadiazolyl, or tetrazolyl, and is substituted with 0-3 substituents selected from halo, cyano, alkyl, haloalkyl, benzyl, alkoxy, haloalkoxy, alkenyloxy, and benzyloxy.

10. A compound of claim 1 where Ar¹ is pyrazolyl substituted with 0-3 substituents selected from halo, cyano, alkyl, haloalkyl, benzyl, alkoxy, haloalkoxy, alkenyloxy, and benzyloxy.

* * * * *